(12) United States Patent
Fantini et al.

(10) Patent No.: US 9,408,598 B1
(45) Date of Patent: Aug. 9, 2016

(54) SYSTEMS AND METHODS FOR ACCESSING AN INTERVERTEBRAL DISC SPACE IN A BODY OF A PATIENT

(71) Applicant: Altus Partners, LLC, Newtown Square, PA (US)

(72) Inventors: Gary A. Fantini, Greenwich, CT (US); Charlie Goodwin, New York, NY (US); Alex Hughes, New York, NY (US); Brian Bankoski, West Grove, PA (US); Michael A. Fitzgerald, Newtown Square, PA (US)

(73) Assignee: Altus Partners, LLC, Newtown Square, PA (US)

( * ) Notice: Subject to any disclaimer, the term of this patent is extended or adjusted under 35 U.S.C. 154(b) by 0 days.

(21) Appl. No.: 14/714,951

(22) Filed: May 18, 2015

(51) Int. Cl.
| | |
|---|---|
| A61B 1/32 | (2006.01) |
| A61B 17/02 | (2006.01) |
| A61B 19/00 | (2006.01) |
| A61F 2/44 | (2006.01) |
| A61F 2/46 | (2006.01) |
| A61B 17/00 | (2006.01) |

(52) U.S. Cl.
CPC ........... *A61B 17/0218* (2013.01); *A61B 17/025* (2013.01); *A61B 17/0206* (2013.01); *A61B 19/26* (2013.01); *A61F 2/4455* (2013.01); *A61F 2/4611* (2013.01); *A61B 2017/00473* (2013.01); *A61B 2017/0262* (2013.01); *A61B 2019/268* (2013.01)

(58) Field of Classification Search
CPC . A61B 17/02; A61B 17/0206; A61B 17/0293
USPC .................................................. 600/201-246
See application file for complete search history.

(56) References Cited

U.S. PATENT DOCUMENTS

| | | | | |
|---|---|---|---|---|
| 5,944,658 | A * | 8/1999 | Koros | A61B 17/0206 600/231 |
| 8,449,463 | B2 | 5/2013 | Nunley et al. | |
| 8,591,432 | B2 * | 11/2013 | Pimenta | A61B 1/32 600/554 |

(Continued)

OTHER PUBLICATIONS

Baxano Surgical, Inc. Announces Two New Patents for VEO Direct Lateral and AxiaLIF Minimally Invasive Interbody Fusion Systems *Baxano Surgical, Inc.* Aug. 5, 2014 07:30 ET [http://globenewswire.com/news-release/2014/08/05/656033/10092899/en/Baxano-Surgical . . . ].

(Continued)

*Primary Examiner* — Ellen C Hammond
*Assistant Examiner* — Christina Negrellirodrigue
(74) *Attorney, Agent, or Firm* — Goodwin Procter LLP

(57) ABSTRACT

A method for accessing an intervertebral disc space in a patient's body involves making an incision in a region of the patient's body that permits access to the psoas muscle, directing a blade of a first dissecting refractor through the incision and such that a distal end of the first dissecting retractor blade is positioned proximate the intervertebral disc space, and directing, independently of the first dissecting retractor blade, a blade of a second dissecting retractor through the incision and such that a distal end of the second dissecting retractor blade is positioned proximate the intervertebral disc space. During their placement within the patient's body, the first and second dissecting retractor blades are employed in a tissue dissection process. Following the positioning of the distal ends of the first and second dissecting retractor blades proximate the intervertebral disc space, the first and second dissecting refractors are coupled to one another.

22 Claims, 28 Drawing Sheets

(56) References Cited

U.S. PATENT DOCUMENTS 8,747,472 B2 6/2014 Ainsworth et al.
8,795,167 B2 * 8/2014 Ainsworth ......... A61B 17/0642
600/222

OTHER PUBLICATIONS

Globus Medical "Direct Look Visualized Lateral Access" 2014 6 pages.

Hardenbrook et al "TranSI VEO system: a novel psoas-sparing device for transpsoas lumbar interbody fusion" Medical Devices: Evidence and Research 2013:6 91-95.

Visualized Lateral Access, 2014, Retrieved from [Online] http://www.globusmedical.com/directlook/ [Retrieved on Apr. 22, 2015].

Yuan et al "Minimally invasive lateral lumbar interbody fusion with direct psoas visualization" Journal of Orthopaedic Surgery and Research 2014, 9:20 http://www.josr-online.com/content/9/1/20.

* cited by examiner

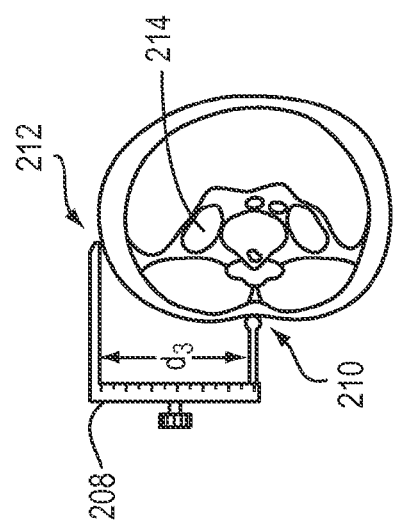
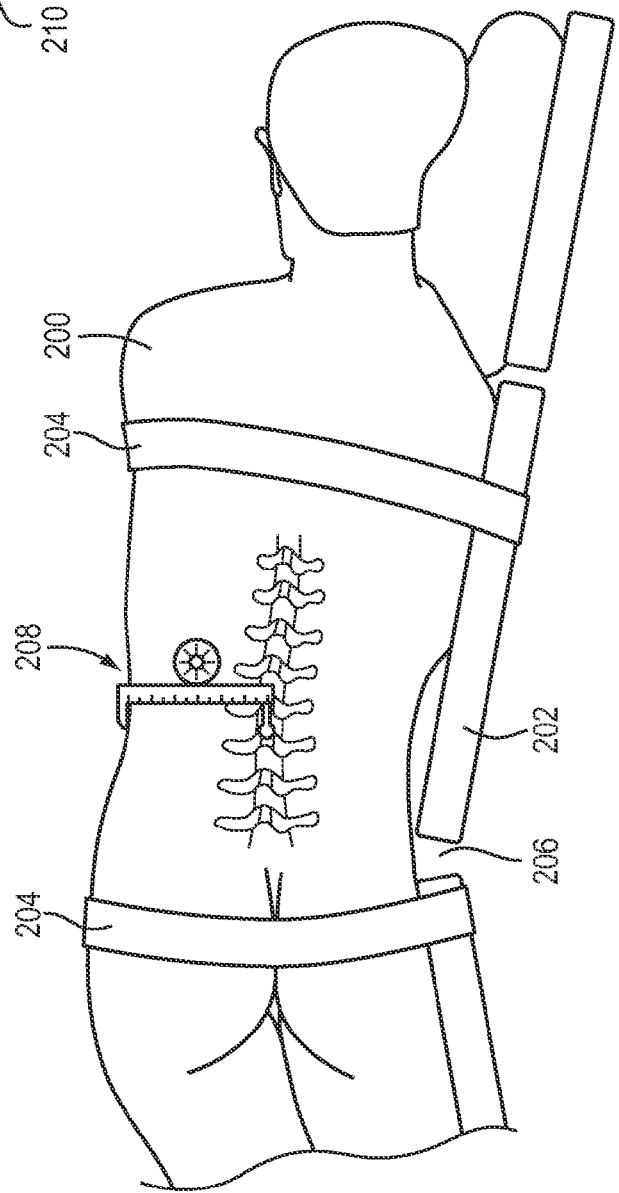
FIG. 4B
FIG. 4A

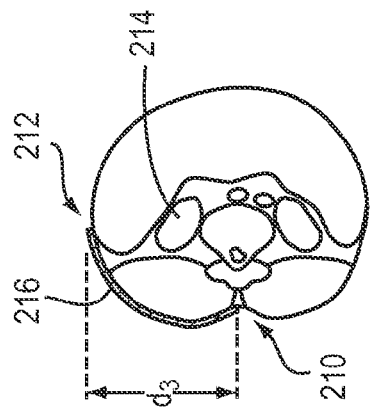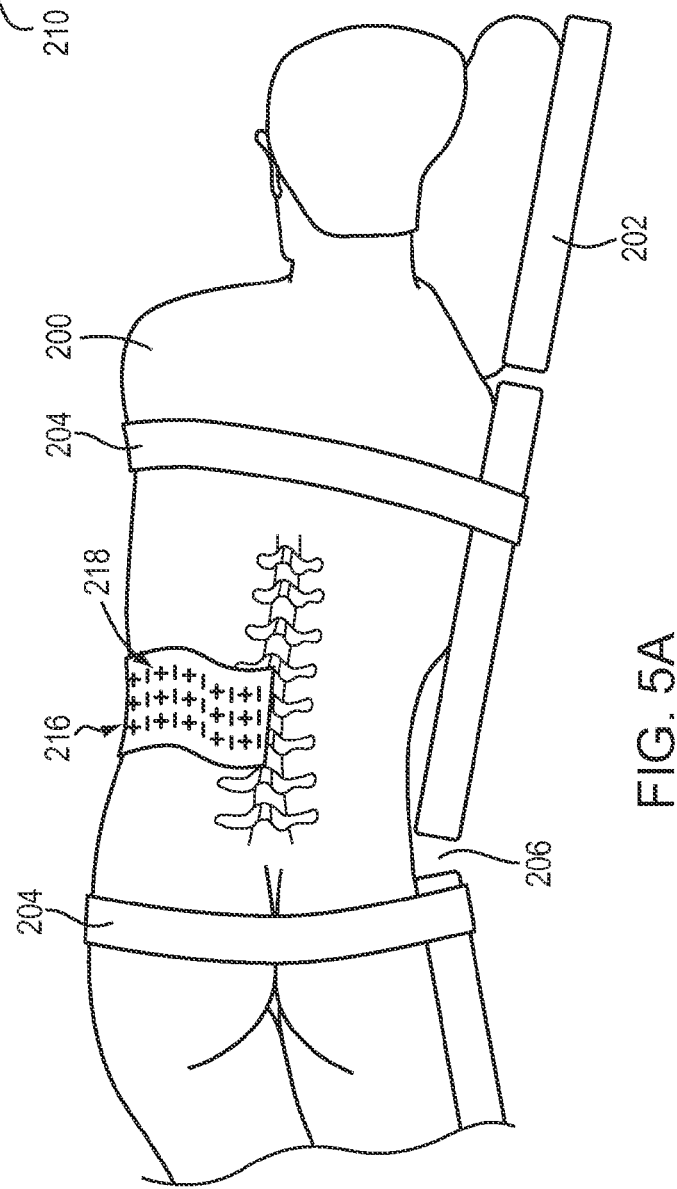

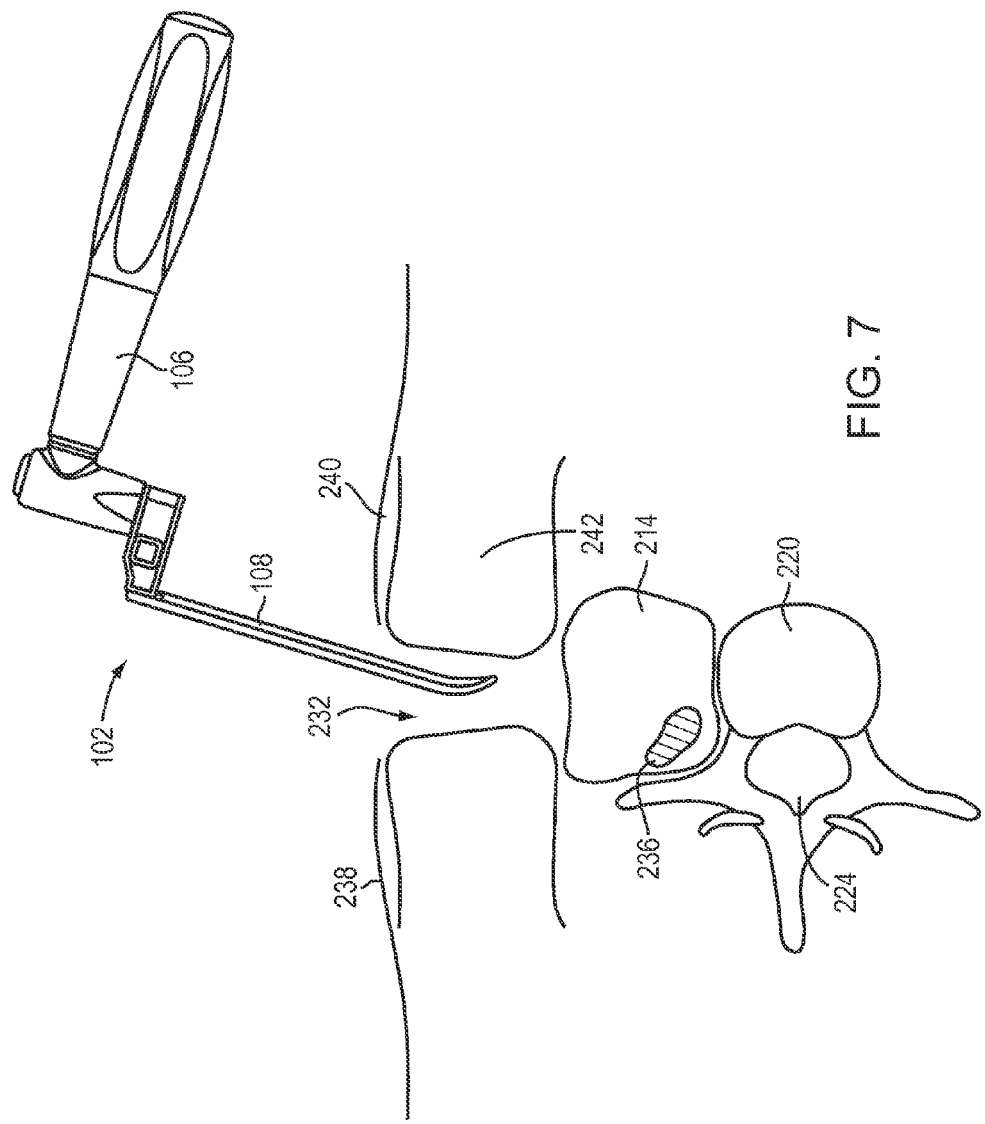

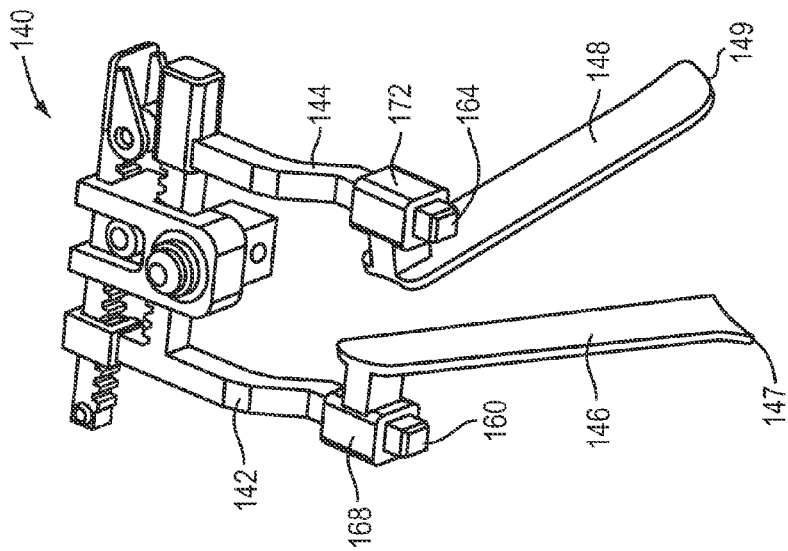
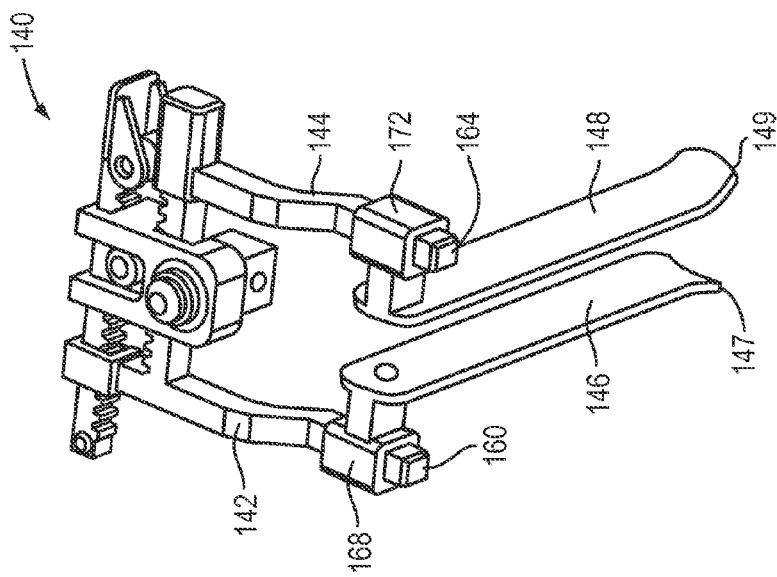

SYSTEMS AND METHODS FOR ACCESSING AN INTERVERTEBRAL DISC SPACE IN A BODY OF A PATIENT

TECHNICAL FIELD

In various embodiments, the present invention relates to systems and methods for accessing an intervertebral disc space in a body of a patient.

BACKGROUND

Fusion surgery can be a viable treatment option for reducing pain and improving function in patients who suffer from chronic lower back pain. In the past, several open and minimally invasive lumbar fusion approaches have been employed by spine surgeons, including anterior lumbar interbody fusion, posterior lumbar interbody fusion, and transforaminal lumbar interbody fusion. Unfortunately, anterior lumbar interbody fusion can endanger major organs and blood vessels, while posterior lumbar interbody fusion and transforaminal lumbar interbody fusion can cause musculoligamentous injury, nerve root injury, and spinal fluid leakage.

To avoid the risks of these injuries, minimally invasive lateral approaches (e.g., a retroperitoneal transpsoas approach) to the lumbar spine have been developed and employed in order to access the intervertebral disc space. One complication to existing lateral approaches, however, is the risk of injuring surrounding nerves, such as those in the lumbar plexus nerve group, which can result in postsurgical motor and sensory deficits (e.g., thigh pain and/or weakness) for the patient. In fact, the wide variability in lumbar plexus anatomy complicates the identification of a safe working zone.

Neuromonitoring may be employed during a lateral approach in an attempt to help identify and avoid surrounding nerves; however, neuromonitoring suffers from its own drawbacks. For example, neuromonitoring can be inaccurate when employed on its own and may lead to a false negative (i.e., falsely indicate that no surrounding nerves are present in the region being accessed), thereby giving the surgeon a false sense of security. Neuromonitoring, moreover, is generally considered to be unreliable. It is not a guarantee against injury, and there is generally no clinical data showing that it prevents injury. In addition, neuromonitoring is time consuming and expensive (both because of the added cost of the neuromonitoring equipment itself and because neuromonitoring complicates and lengthens the surgical procedure). Neuromonitoring is also infeasible if a patient has been temporarily paralyzed and, thus, it inhibits the use of muscle relaxants. Not being able to use muscle relaxants, however, makes fusion surgery more difficult, as the patient's muscles will naturally fight the surgeon's attempt to access, via a channel through those muscles, the lumbar spine.

Another shortcoming to existing lateral approaches to the lumbar spine is the inherent risk of inadvertently closing the access or working channel during the surgical procedure. In particular, the dissecting retractors employed in current procedures to dissect the patient's tissue (e.g., handheld Deaver retractors) are typically removed from the patient's body during the surgery and replaced by self-retaining, expandable retractors that aid in creating the working channel. The process of removing the dissecting retractors and replacing them with self-retaining, expandable retractors often, and disadvantageously, leads to a loss of the established access channel. Repeated dissection is therefore often needed in order to re-establish the access channel, which puts the patient at an increased risk of damage to associated structures. Having to re-establish the access channel also leads to further risk of damage to the patient's neural elements and increased time in the operating room.

Accordingly, there is a need to improve existing lateral approaches to the lumbar spine and, consequently, to develop new surgical tools that facilitate those improved approaches.

SUMMARY OF THE INVENTION

In various embodiments, the present invention features a lateral approach for lumbar interbody fusion that allows for direct visualization of the psoas muscle and surrounding nerves. The direct visualization of the psoas muscle, together with a manual palpation thereof by the surgeon, leads to improved patient safety. In particular, the technique described herein allows the surgeon to identify and avoid the region in the psoas muscle containing the lumbar plexus nerve group, optionally without any neuromonitoring.

In addition, in various embodiments of the present invention, the dissecting retractors that are employed in dissecting the patient's tissue (e.g., the psoas muscle) in order to gain access to the intervertebral disc space convert to self-retaining, expandable retractors that may be manipulated to create the working channel in the patient's body. In other words, the need to remove the dissecting retractors from the patient's body during the surgery and replace them with separate self-retaining, expandable retractors is obviated. Advantageously, this avoids the risk of access or working channel closure during the surgery and the downfalls associated therewith.

In general, in one aspect, embodiments of the invention feature a method for accessing an intervertebral disc space in a body of a patient. The method involves making an incision in a region of the patient's body that permits access to the psoas muscle, directing a blade of a first dissecting retractor through the incision and such that a distal end of the first dissecting retractor blade is positioned proximate the intervertebral disc space, and directing, independently of the first dissecting retractor blade, a blade of a second dissecting retractor through the incision and such that a distal end of the second dissecting retractor blade is positioned proximate the intervertebral disc space. During their placement within the patient's body, the first and second dissecting retractor blades are employed in a tissue dissection process in order to gain access to the intervertebral disc space, and, following the positioning of the distal ends of the first and second dissecting retractor blades proximate the intervertebral disc space, the first and second dissecting retractors are coupled to one another.

In various embodiments, the method further involves manually palpating the psoas muscle subsequent to making the incision in the region of the patient's body. The first dissecting retractor blade may be directed anterior to, or through, the psoas muscle. For its part, the second dissecting retractor blade may be positioned posterior to the first dissecting retractor blade. In general, the first and second dissecting retractor blades are both directed to avoid a region in the psoas muscle comprising a lumbar plexus nerve group.

In one embodiment, coupling the first and second dissecting retractors to one another involves coupling a retractor stabilizing frame to both the first and second dissecting retractors. Subsequently, a handle may be removed from each of the first and second dissecting retractors. In addition, a stabilizing arm may be coupled to the retractor stabilizing frame and to a rigid structure, such as an operating table. In one embodiment, the retractor stabilizing frame includes a translation mechanism for adjusting a spacing between the first and second dissecting retractor blades. A size of a working channel defined within the patient's body may be adjusted by manipulating the translation mechanism.

In certain embodiments, third and fourth blades are directed through the incision and such that distal ends of the third and fourth blades are positioned proximate the intervertebral disc space. The third and fourth blades may both be coupled to a blade stabilization frame, which may include a translation mechanism for adjusting a spacing between the third and fourth blades. In one embodiment, the method further involves coupling the blade stabilization frame to at least one of the first and second dissecting retractors and/or adjusting a size of a working channel defined within the patient's body by manipulating the translation mechanism.

In various embodiments, the method further involves directing a surgical instrument (e.g., an intervertebral fusion cage inserter) through the incision and to the intervertebral disc space and/or delivering a surgical implant (e.g., an intervertebral fusion cage) through the incision and to the intervertebral disc space. The method may also include targeting a desired surgical level and sizing lengths of the first and second dissecting retractor blades prior to making the incision, for example by using a measurement caliper.

In general, in another aspect, embodiments of the invention feature a system for use in accessing an intervertebral disc space in a body of a patient. The system includes a first dissecting retractor, a second dissecting retractor, and a retractor stabilizing frame. The first dissecting retractor includes a first blade and a first removable handle, while the second dissecting retractor includes a second blade and a second removable handle. The refractor stabilizing frame is for attachment to both the first and second dissecting retractors subsequent to placement of the first and second blades within the patient's body.

In various embodiments, the retractor stabilizing frame includes a translation mechanism for adjusting a spacing between the first and second blades. The system may also include a driver for manipulating the translation mechanism. In addition, the system may include a stabilizing arm for attachment to the retractor stabilizing frame and to a rigid structure. Moreover, the system may include a blade stabilization frame for attachment to at least one of the first and second dissecting retractors following removal of at least one of the first and second handles. The blade stabilization frame may include third and fourth blades and/or a translation mechanism for adjusting a spacing between the third and fourth blades. Again, the system may also include a driver for manipulating that translation mechanism.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 4A is a schematic side view of a patient illustrating how desired surgical levels may be targeted with adjustable non-invasive measurement calipers in accordance with one embodiment of the invention;

FIG. 4B is a schematic axial view of a patient's lumbar spine illustrating how desired surgical levels may be targeted with adjustable non-invasive measurement calipers in accordance with one embodiment of the invention;

FIG. 5A is a schematic side view of a patient illustrating how desired surgical levels may be targeted with a non-invasive, flexible target mat in accordance with one embodiment of the invention;

FIG. 5B is a schematic axial view of a patient's lumbar spine illustrating how desired surgical levels may be targeted with a non-invasive, flexible target mat in accordance with one embodiment of the invention;

FIGS. 7-13 schematically illustrate various exemplary steps in a method for accessing an intervertebral disc space in a body of a patient in accordance with one embodiment of the invention;

FIGS. 23A and 23B schematically illustrate a "toe-in" capability for the blades of the optional blade stabilization frame of FIG. 21 in accordance with one embodiment of the invention;

DESCRIPTION

In various embodiments, the present invention features systems and methods for accessing an intervertebral disc space in a body of a patient. In particular, a minimally invasive lateral transpsoas approach is employed for lumbar interbody fusion. The approach allows for direct visualization of the psoas muscle and surrounding nerves, permitting the surgeon to identify and avoid the region in the psoas muscle containing the lumbar plexus nerve group without, optionally, any neuromonitoring. In accessing the lumbar spine, the surgeon may employ dissecting retractors to dissect the patient's tissue (e.g., the psoas muscle). Advantageously, those dissecting retractors thereafter convert to self-retaining, expandable retractors that may be employed in creating a working channel in the patient's body, thereby obviating the need to remove the dissecting retractors from the patient's body during the surgery and to replace them with separate self-retaining, expandable retractors. The risk of access or working channel closure during the surgery is, consequently, greatly diminished.

Figure 1:
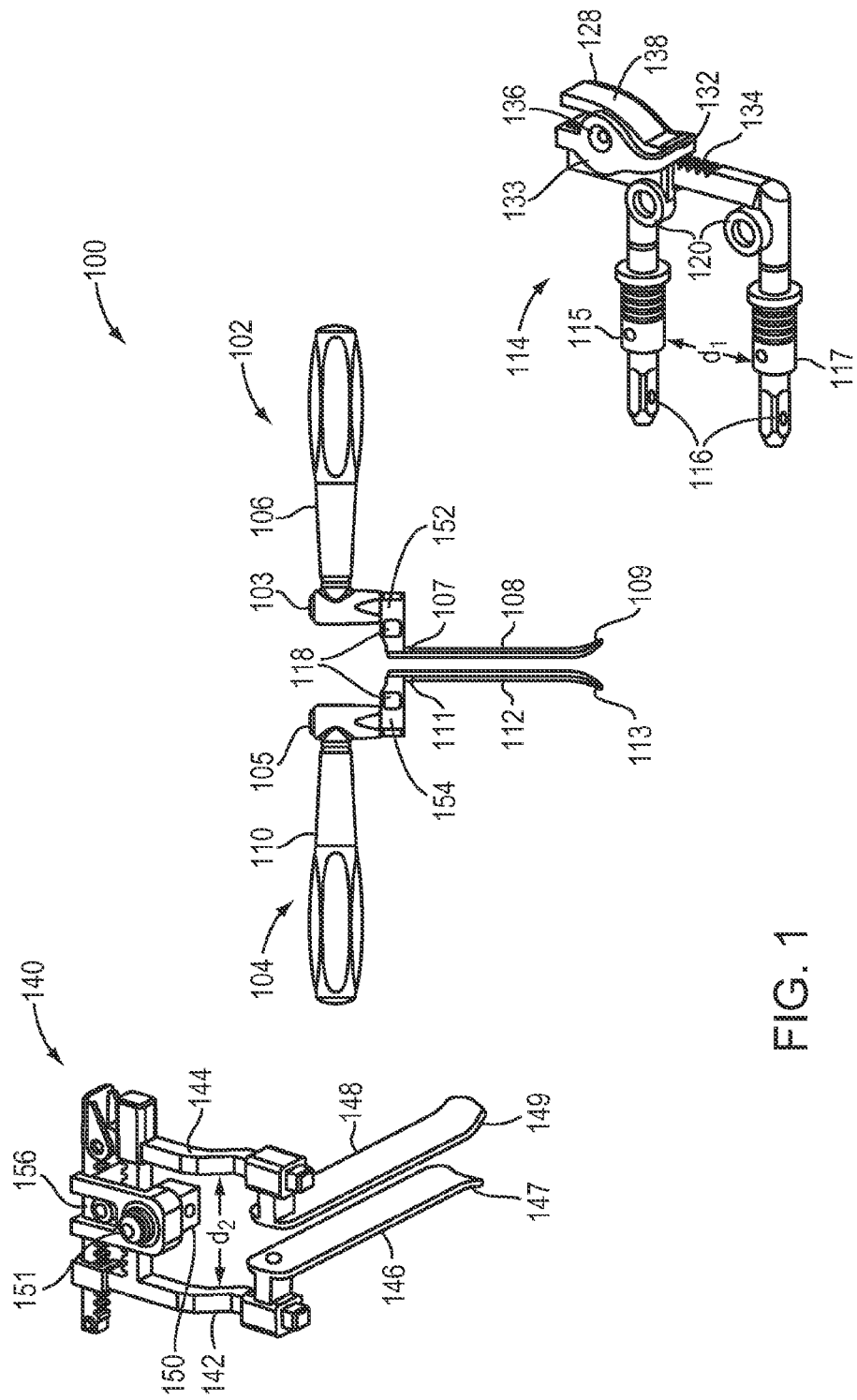
FIG. 1 is a schematic view of a partially assembled system for accessing an intervertebral disc space in a patient's body in accordance with one embodiment of the invention.

FIG. 1 depicts a schematic view of one embodiment of a partially assembled system 100 for accessing the intervertebral disc space in the patient's body. As shown, the system 100 includes a first dissecting retractor 102 and a second dissecting retractor 104. The first dissecting retractor 102 includes a first handle 106 and a first blade 108 having a proximal end 107 and a distal end 109. Similarly, the second dissecting retractor 104 includes a second handle 110 and a second blade 112 having a proximal end 111 and a distal end 113. As further explained below, each of the first and second handles 106, 110 is removable from its respective dissecting retractor 102, 104. The handles 106, 110 may, for example, include detachment mechanisms 103, 105 (e.g., push-button releases) to facilitate their release from their respective dissecting refractor 102, 104.

The system 100 also includes a retractor stabilizing frame 114 for attachment to both the first and second dissecting retractors 102, 104 subsequent to placement, as described below, of the first and second blades 108, 112 within the patient's body. As illustrated, the retractor stabilizing frame 114 includes two legs 115, 117 and blade attachment fittings 116 at the ends of the legs 115, 117 for coupling the retractor stabilizing frame 114 to the first and second dissecting retractors 102, 104. To that end, the dissecting retractors 102, 104 may each include a corresponding fitting 118 for mating with one of the blade attachment fittings 116. The blade attachment fittings 116 may be snap fittings configured to snap into connection with the corresponding fittings 118. Other types of fittings may also be employed, as will be understood by one of ordinary skill in the art.

The retractor stabilizing frame 114 also includes stabilizing arm attachment points 120 for attaching a stabilizing arm 122. For simplicity, the stabilizing arm 122 is not illustrated in FIG. 1. The stabilizing arm 122 is, however, illustrated in FIG. 2, where it is shown as being connected at its distal end 124 to one of the attachment points 120 of the retractor stabilizing frame 114. The retractor stabilizing frame 114 is illustrated in FIGS. 1 and 2 as having two attachment points 120 for the stabilizing arm 122, but the frame 114 may instead feature fewer (e.g., one) or more (e.g., three) attachment points for the stabilizing arm 122.

The stabilizing arm 122 may be coupled to the retractor stabilizing frame 114 in any of a variety of manners. For example, the stabilizing arm attachment point(s) 120 may be grooved and the stabilizing arm 122 may be screwed into an attachment point 120. As another example, a force fit may be employed to couple the stabilizing arm 122 to the retractor stabilizing frame 114. A proximal end 126 of the stabilizing arm 122 may include a clamp (not shown) or other attachment mechanism for attaching the stabilizing arm 122 to a rigid structure, such as an operating table.

Figure 2:
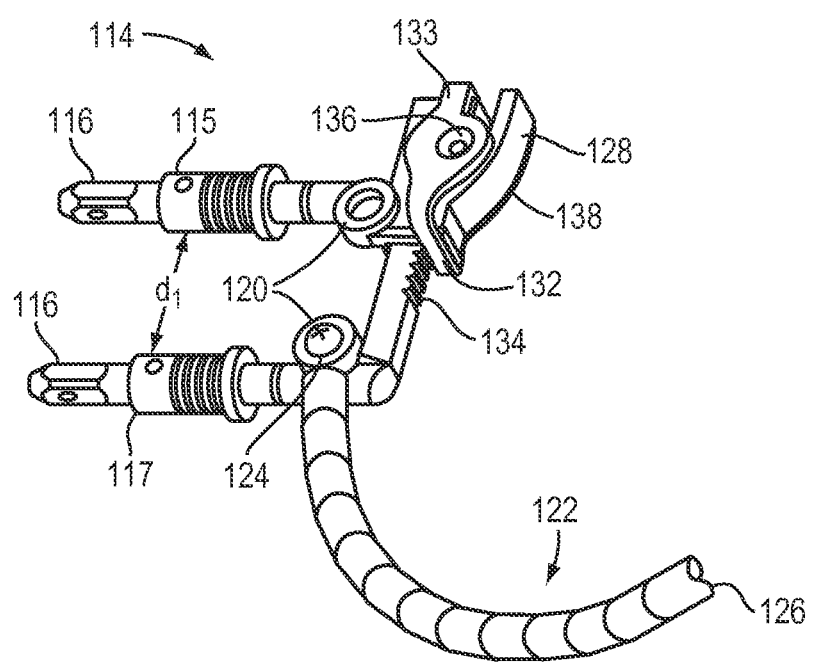
FIG. 2 is a schematic view of a stabilizing arm connected to a stabilizing frame in accordance with one embodiment of the invention.
Figure 18:
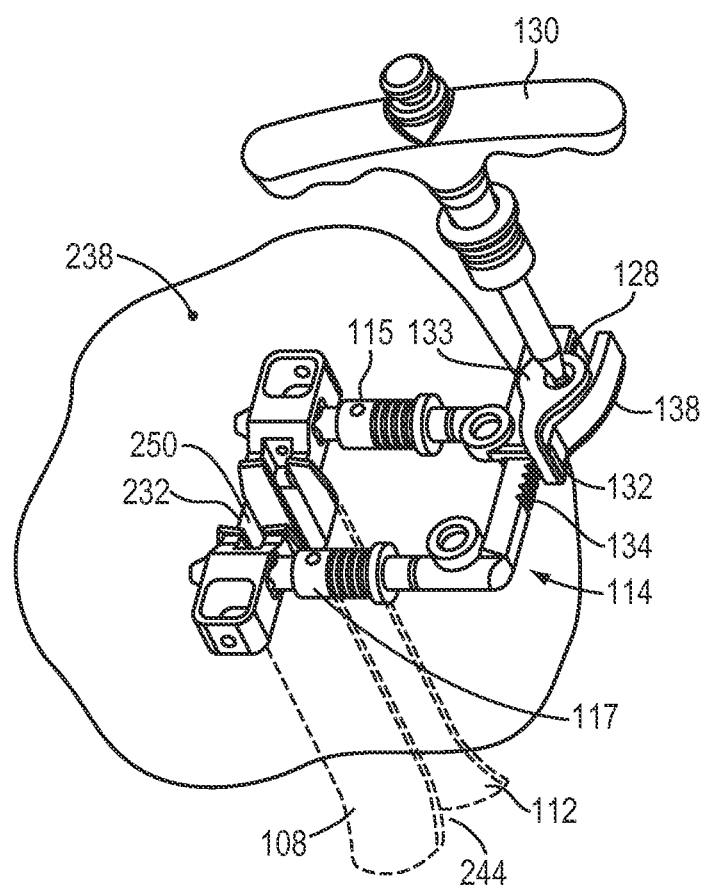
FIG. 18 schematically illustrates the use of a handheld driver to actuate a translation mechanism of a retractor stabilizing frame and thereby adjust a size of a working channel in a patient's body in accordance with one embodiment of the invention.

The retractor stabilizing frame 114 may also include, as shown in FIGS. 1 and 2, a translation mechanism 128 for adjusting a spacing between the first and second blades 108, 112. In one embodiment, a driver 130 (see FIG. 18) is employed to manipulate the translation mechanism 128 to vary a distance $d_1$ between the two legs 115, 117 of the retractor stabilizing frame 114 and, accordingly, the spacing between the first and second blades 108, 112 when the blade attachment fittings 116 are coupled to the corresponding fittings 118 of the dissecting retractors 102, 104. In one particular embodiment, the translation mechanism 128 is a rack and pinion assembly that features a pinion 133 and a linear rack of teeth 134. The translation mechanism 128 also includes a spring-loaded pawl 132 for engaging the linear rack of teeth 134 to maintain the position of the rack 134. In one such embodiment, the driver 130 (which may be a handheld driver 130, as illustrated in FIG. 18) may be inserted into a receptacle 136 of the pinion 133 and rotated to linearly translate the rack of teeth 134, thereby increasing the distance $d_1$ and the spacing between the first and second blades 108, 112. As this occurs, the spring-loaded pawl 132 passes over each successive tooth in the linear rack of teeth 134. The pawl 132 engages the teeth in the rack 134, thereby preventing the distance $d_1$ and the spacing between the first and second blades 108, 112 from decreasing. The translation mechanism 128 may also feature an expansion release lever 138 to disengage the pawl 132 from the rack of teeth 134, thereby permitting the surgeon to collapse the distance $d_1$ and the spacing between the first and second blades 108, 112.

With reference again to FIG. 1, the system 100 also includes a blade stabilization frame 140. The blade stabilization frame 140 includes two legs 142, 144. As illustrated, a third blade 146 is coupled to one leg 142, and a fourth blade 148 is coupled to the other leg 144. The third and fourth blades 146, 148 include distal ends 147, 149. In addition, the blade stabilization frame 140 may include an attachment mechanism 150 for attaching the frame 140 to either the first or second dissecting retractor 102, 104.

In one particular embodiment, the first dissecting retractor 102 includes a first attachment interface 152 to which the first removable handle 106 may be attached (e.g., via a snap fit, a force fit, or other suitable connection), and the second dissecting retractor 104 includes a second attachment interface 154 to which the second removable handle 110 may be attached (e.g., via a snap fit, a force fit, or other suitable connection). As can be seen by comparing FIG. 21 to FIG. 22 and as further described below, following removal of either or both handles 106, 110, the attachment mechanism 150 of the blade stabilization frame 140 may be attached (e.g., via a snap fit, a force fit, or other suitable connection) to one of the first and second attachment interfaces 152, 154 in order to couple the blade stabilization frame 140 to either the first dissecting retractor 102 or the second dissecting retractor 104. With reference again to FIG. 1, the blade stabilization frame 140 may also include a detachment mechanism 151 (e.g., a push-button release) to facilitate the release of the blade stabilization frame 140 from an attachment interface 152, 154 of a refractor 102, 104.

In a similar fashion to the retractor stabilizing frame 114, the blade stabilization frame 140 may also include a translation mechanism 156 for adjusting a spacing between the third and fourth blades 146, 148. As before, the translation mechanism 156 may be a rack and pinion assembly that interacts with a spring-loaded pawl. A driver similar to the driver 130 illustrated in FIG. 18 may be employed to manipulate the translation mechanism 156 to increase a distance $d_2$ between the legs 142, 144, thereby also increasing a spacing between the third and fourth blades 146, 148. The translation mechanism 156 may also include an expansion release lever for disengaging the pawl and thereby permitting a surgeon to collapse the distance $d_2$ and the spacing between the third and fourth blades 146, 148.

Figure 3:
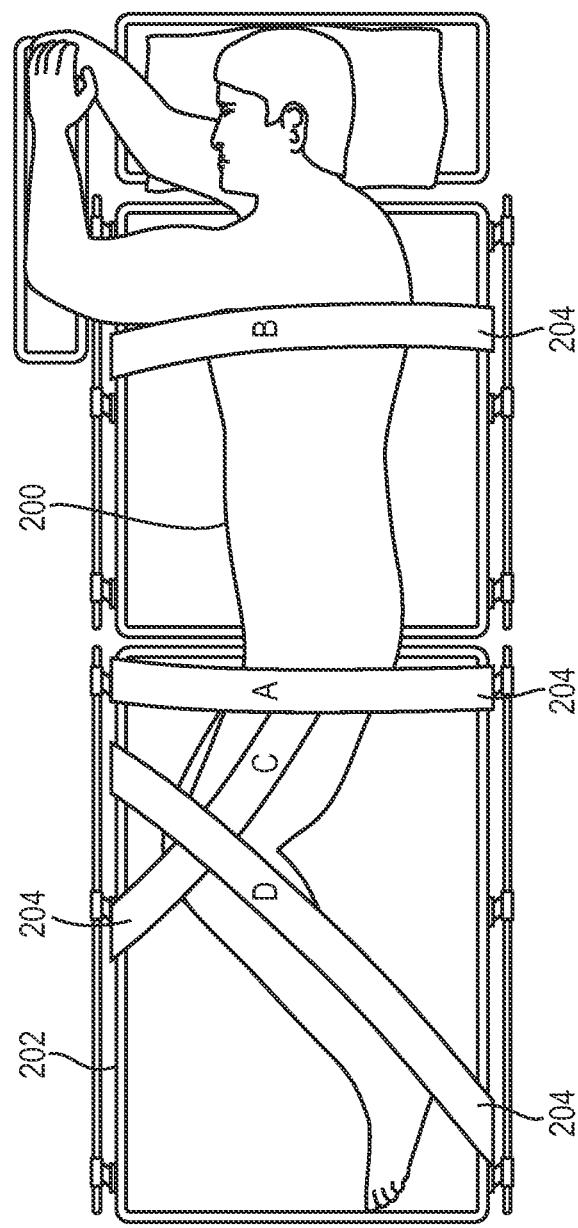
FIG. 3 is a schematic view of a patient positioned in a lateral decubitus position on an initially flat breaking table in accordance with one embodiment of the invention.

Having described the exemplary system 100, an exemplary method for accessing an intervertebral disc space in a body of a patient using the system 100 will now be described. With reference to FIG. 3, the patient 200 is first positioned in a lateral decubitus position on an initially flat breaking table 202 (e.g., a radiolucent breaking table 202) with the hips and knees slightly bent in order to relax the psoas muscle. As illustrated, the patient 200 may then be secured to the table 202 with tape 204. In one embodiment, the tape 204 is applied (A) just below the iliac crest, (B) over the thoracic region, (C) from the iliac crest to the knee to the table 202, and (D) from the table 202 over the knee and ankle to the table 202. Next, true anteroposterior and lateral images (e.g., radiographs) may be obtained to ensure proper positioning of the patient 200. As illustrated in FIGS. 4A and 5A, once the proper positioning of the patient 200 is confirmed, the table 202 may be broken (i.e., bent at inflexion point 206) to facilitate access to the lateral spine.

Prior to making an incision in the patient 200, the desired surgical levels may be targeted, and the lengths of the blades 108, 112 of the first and second dissecting retractors 102, 104 (as well as the lengths of the third and fourth blades 146, 148 of the blade stabilization frame 140) may be sized. For example, as illustrated in FIGS. 4A and 4B, the desired surgical levels may be targeted with adjustable non-invasive measurement calipers 208. In particular, the calipers 208 may be employed to measure a distance $d_3$ between a centerline of the patient's spine 210 and a level 212 of the incision to be made on the patient's skin above the psoas muscle 214. In one embodiment, the non-invasive measurement calipers 208 are adjustable to match patient 200 size so that both the depth to the surgical site (as represented by the distance $d_3$) and the required lengths of the first and second dissecting retractor blades 108, 112 (as well as the required lengths of the third and fourth blades 146, 148 of the blade stabilization frame 140) may be determined. X-rays may also be taken to verify the surgical levels and the depth to the surgical site.

As an alternative to employing the calipers 208, the desired surgical levels may instead be targeted with a non-invasive, flexible target mat 216, as illustrated in FIGS. 5A and 5B. The target mat 216 may be disposable (e.g., intended for one-time use) or reusable (e.g., sterilizable). In addition, the target mat 216 may include radiographic targeting and measurement markings 218 to aid in determining both the depth to the surgical site (i.e., the distance $d_3$ between the centerline of the patient's spine 210 and the level 212 of the incision to be made on the patient's skin above the psoas muscle 214) and the required lengths of the first and second dissecting retractor blades 108, 112 (as well as the required lengths of the third and fourth blades 146, 148 of the blade stabilization frame 140).

Once the depth to the surgical site, the required lengths of the first and second dissecting retractor blades 108, 112, and the required lengths of the third and fourth blades 146, 148 of the blade stabilization frame 140 are determined, the surgeon may make an incision in a region of the patient's body that permits access to the psoas muscle 214. For example, the surgeon may make the incision in the patient's skin at a point slightly ventral to the patient's erector spinae muscles. Subsequent to making the incision, the surgeon may manually palpate the psoas muscle 214 (e.g., with the surgeon's finger) as an aid to localizing the patient's intervertebral disc space.

Figure 6A:
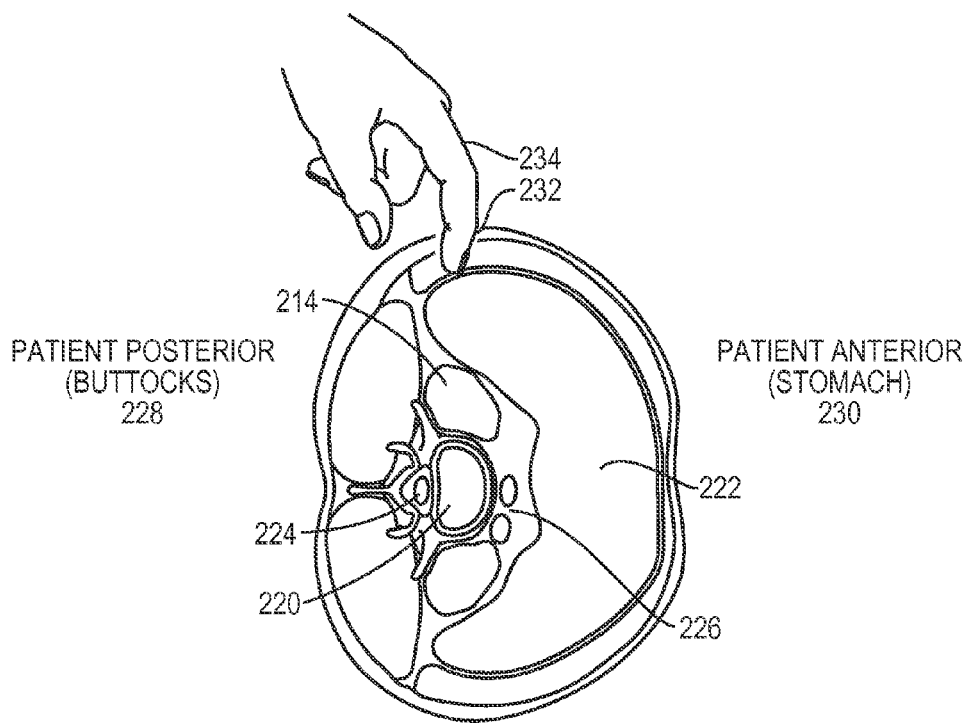
FIGS. 6A and 6B are schematic axial views of a patient's lumbar spine illustrating the steps undertaken by a surgeon in order to manually palpate the patient's psoas muscle in accordance with one embodiment of the invention.
Figure 6B:
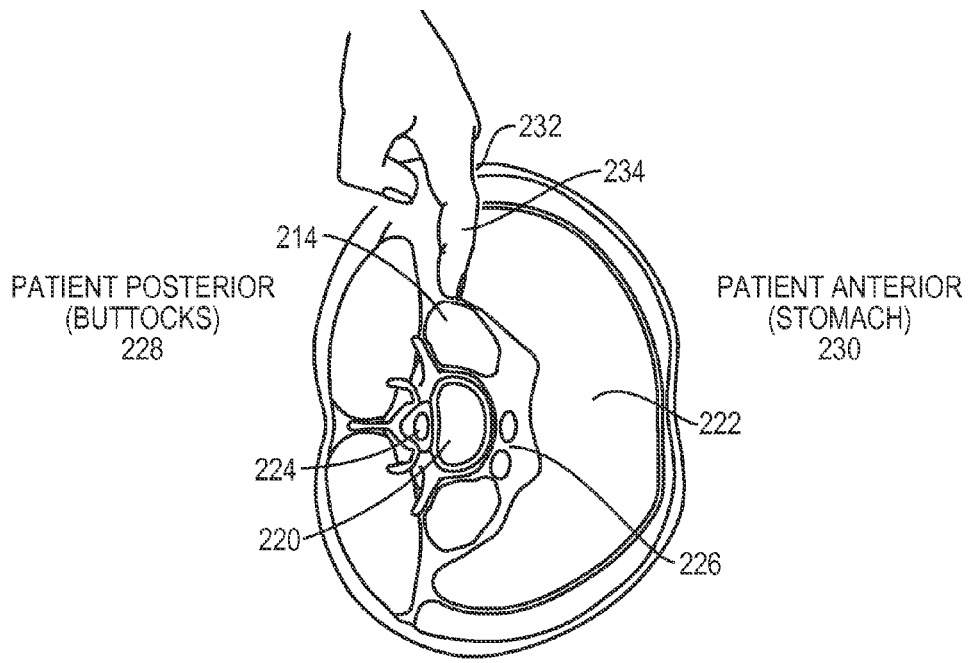

FIGS. 6A and 6B are schematic axial views of a patient's lumbar spine illustrating the just described manual palpation of the psoas muscle 214 in accordance with one embodiment of the invention. In particular, FIGS. 6A and 6B depict the patient's psoas muscle 214, intervertebral disc space 220, peritoneal cavity 222, axial foramen and spinal canal 224, and great vessels 226. Also demarcated are the patient's posterior (i.e., buttocks) 228 and anterior (i.e., stomach) 230. As illustrated in FIG. 6A, the surgeon initially approaches the psoas muscle 214 through the skin incision 232 with his or her finger 234. The manual palpation through the skin incision (FIG. 6A) then progresses to a manual palpation of (and, optionally, into) the psoas major muscle 214, as illustrated in FIG. 6B. In one embodiment, the approach of the surgeon's finger 234 in FIG. 6B is anterior to the region of the lumbar plexus nerve group 236 (first illustrated in FIG. 7). This process allows key anatomical landmarks to be palpated, verified, and localized.

Following this manual palpation, and as illustrated in FIGS. 7-13, the surgeon may direct the first blade 108 of the first dissecting retractor 102 through the skin incision 232 and such that the distal end 109 of the first dissecting retractor blade 108 is positioned proximate the intervertebral disc space 220. Similarly, the second blade 112 of the second dissecting retractor 104 may be directed by the surgeon, independently of the first dissecting retractor blade 108, through the skin incision 232 and such that the distal end 113 of the second dissecting retractor blade 112 is positioned proximate the intervertebral disc space 220.

Figure 8:
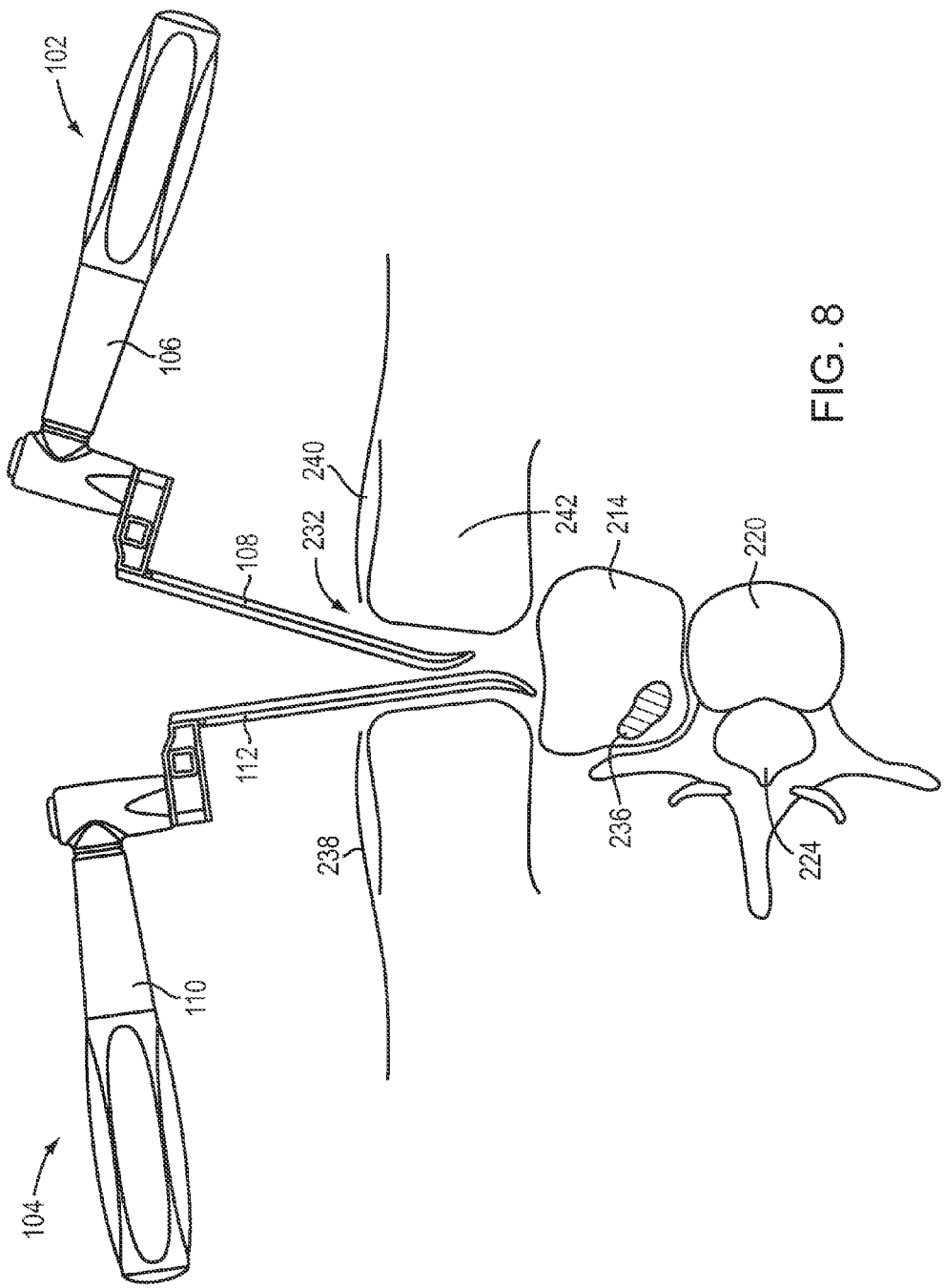
Figure 9:
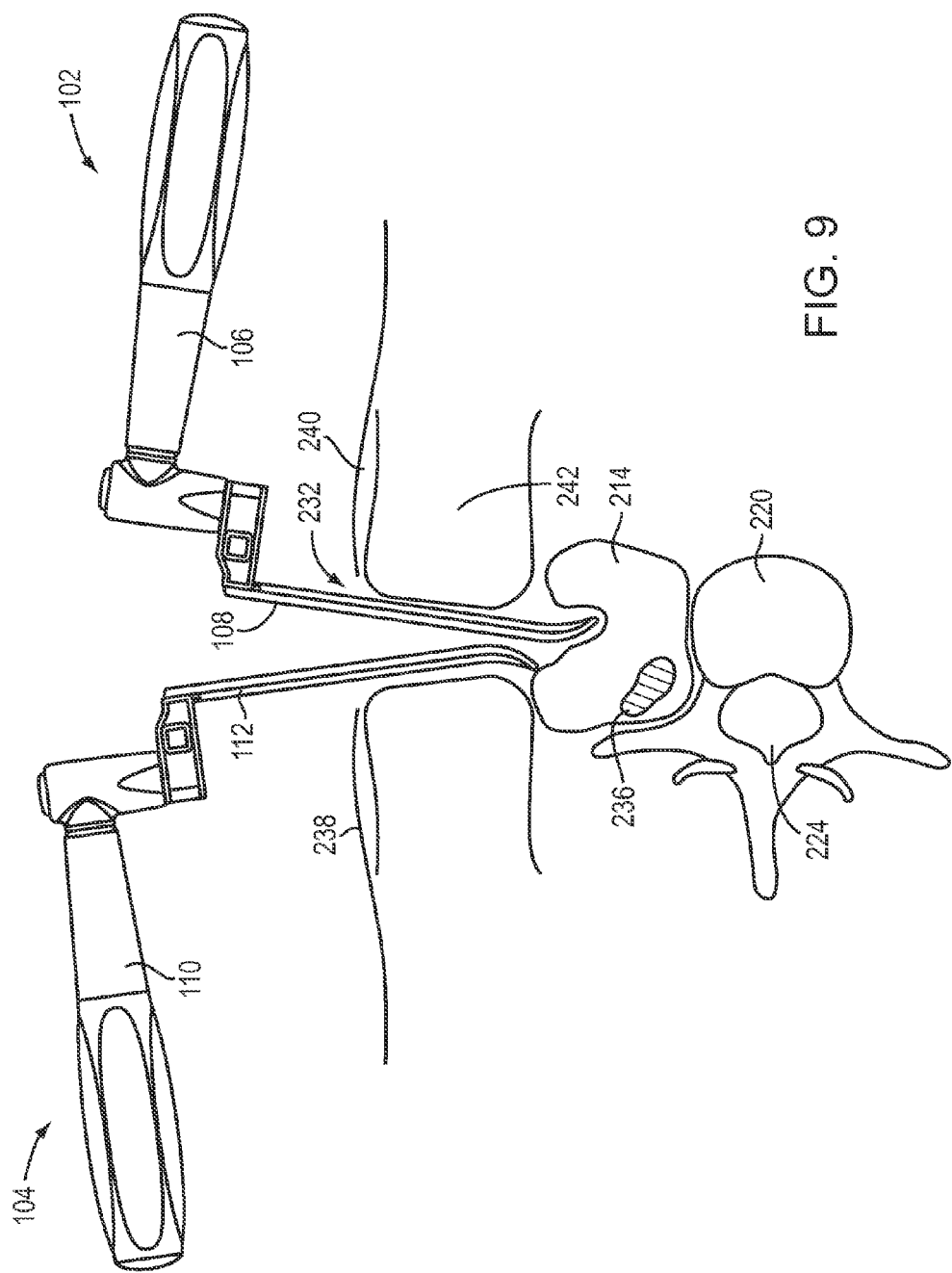
Figure 10:
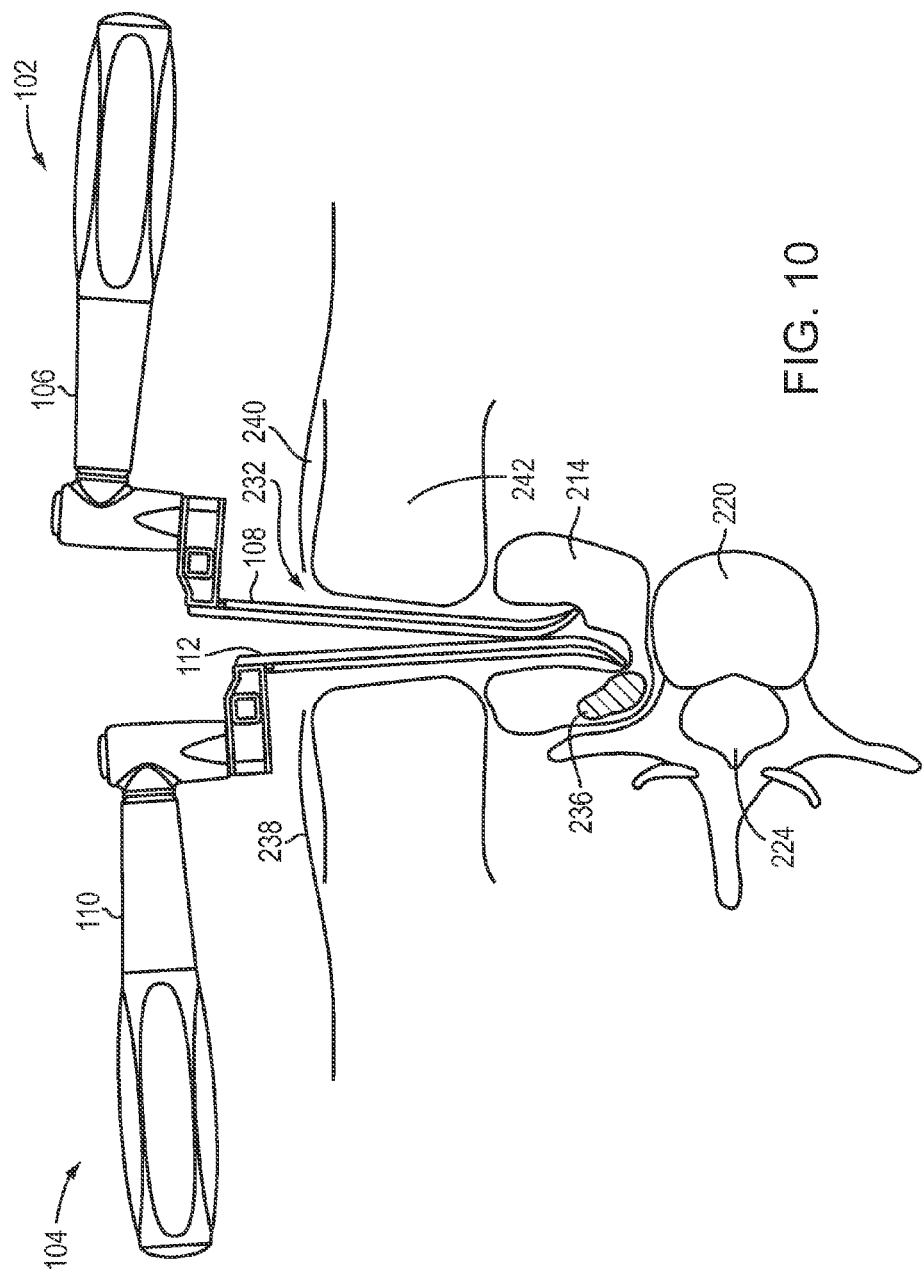
Figure 11:
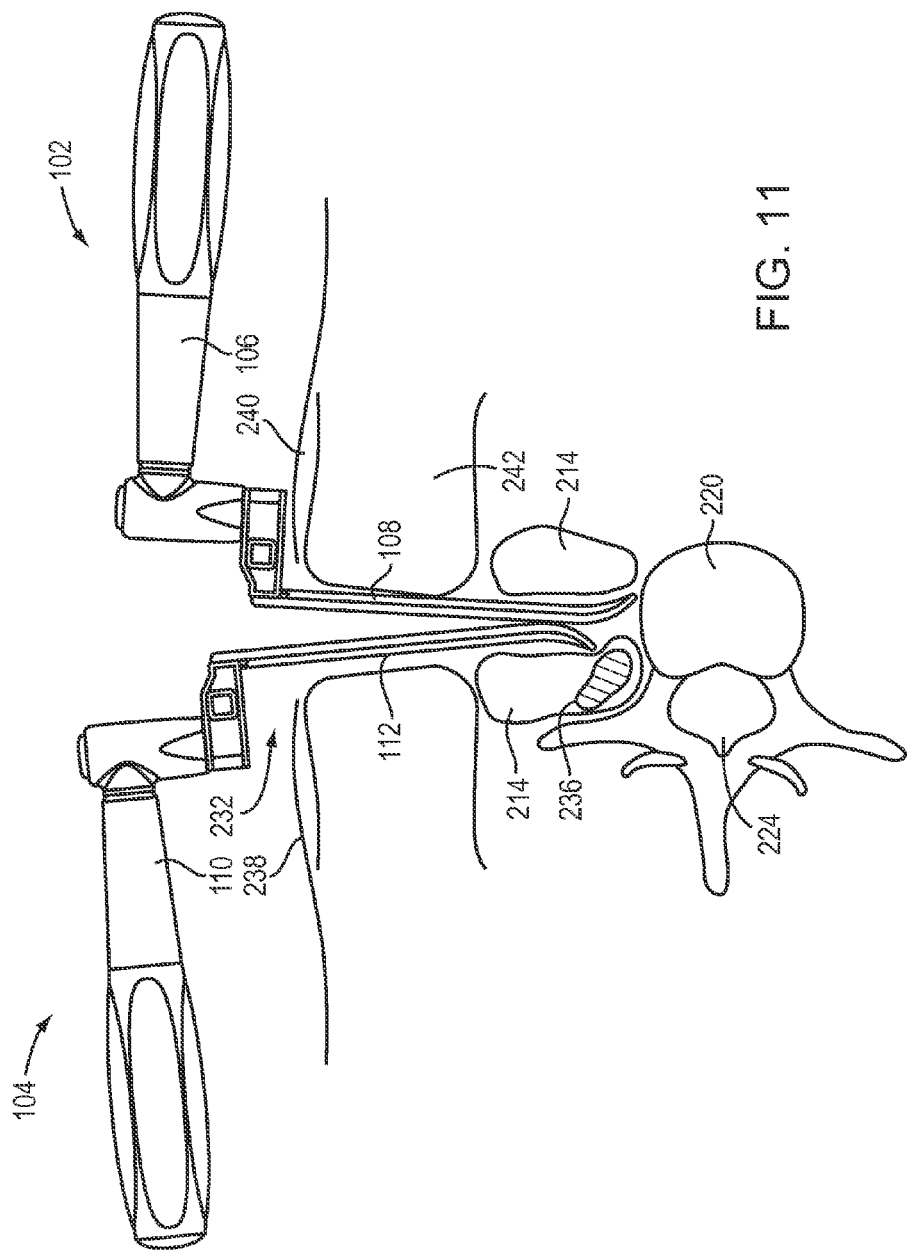

In greater detail, as illustrated in FIG. 7, the first blade 108 of the first dissecting retractor 102 is introduced (e.g., manually, using the first removable handle 106) into the incision 232 through the patient's skin level 238, subdermal layer 240, and subdermal tissues 242 and is directed towards a working area lateral to the intervertebral disc space 220. As illustrated in FIG. 8, the second blade 112 of the second dissecting retractor 104 may also be introduced (e.g., manually, using the second removable handle 110) posterior to the first dissecting retractor blade 108 and into the incision 232 through the patient's skin level 238, subdermal layer 240, and subdermal tissues 242. The first and second dissecting retractor blades 108, 112 may then be employed, during their placement within the patient's body, in a tissue dissection process in order to gain access to the intervertebral disc space 220. For example, the first and second dissecting retractor blades 108, 112 may be alternately advanced, as illustrated in FIG. 8, to dissect the subdermal tissues 242. Similarly, the first and second dissecting retractor blades 108, 112 may be alternately advanced, as illustrated in FIGS. 9 through 11, into the psoas muscle 214 anterior to the region of the lumbar plexus nerve group 236 until the psoas muscle 214 is completely separated down to the level of the surgical site 244.

In an alternative embodiment, rather than directing the first and second dissecting retractor blades 108, 112 through the psoas muscle 214, the surgeon instead directs the blades 108, 112 anterior to the psoas muscle 214. The surgeon's decision on how to approach the intervertebral disc space 220 may depend, in part, on the level of the patient's spine. In either case, through direct visualization and manual palpation of the psoas muscle 214, the surgeon is advantageously able to carefully direct both the first and second dissecting retractor blades 108, 112 to avoid the region of the lumbar plexus nerve group 236 in the psoas muscle 214. As a result, the surgeon is able to reduce the likelihood of postsurgical motor and sensory deficits (e.g., thigh pain and/or weakness) being experienced by the patient without, optionally, any neuromonitoring. Advantageously, by not having to employ neuromonitoring, the surgeon is also free to use muscle relaxants during the surgical procedure and to temporarily paralyze the patient, thereby making it easier for the surgeon to access the patient's intervertebral disc space 220.

Figure 12:
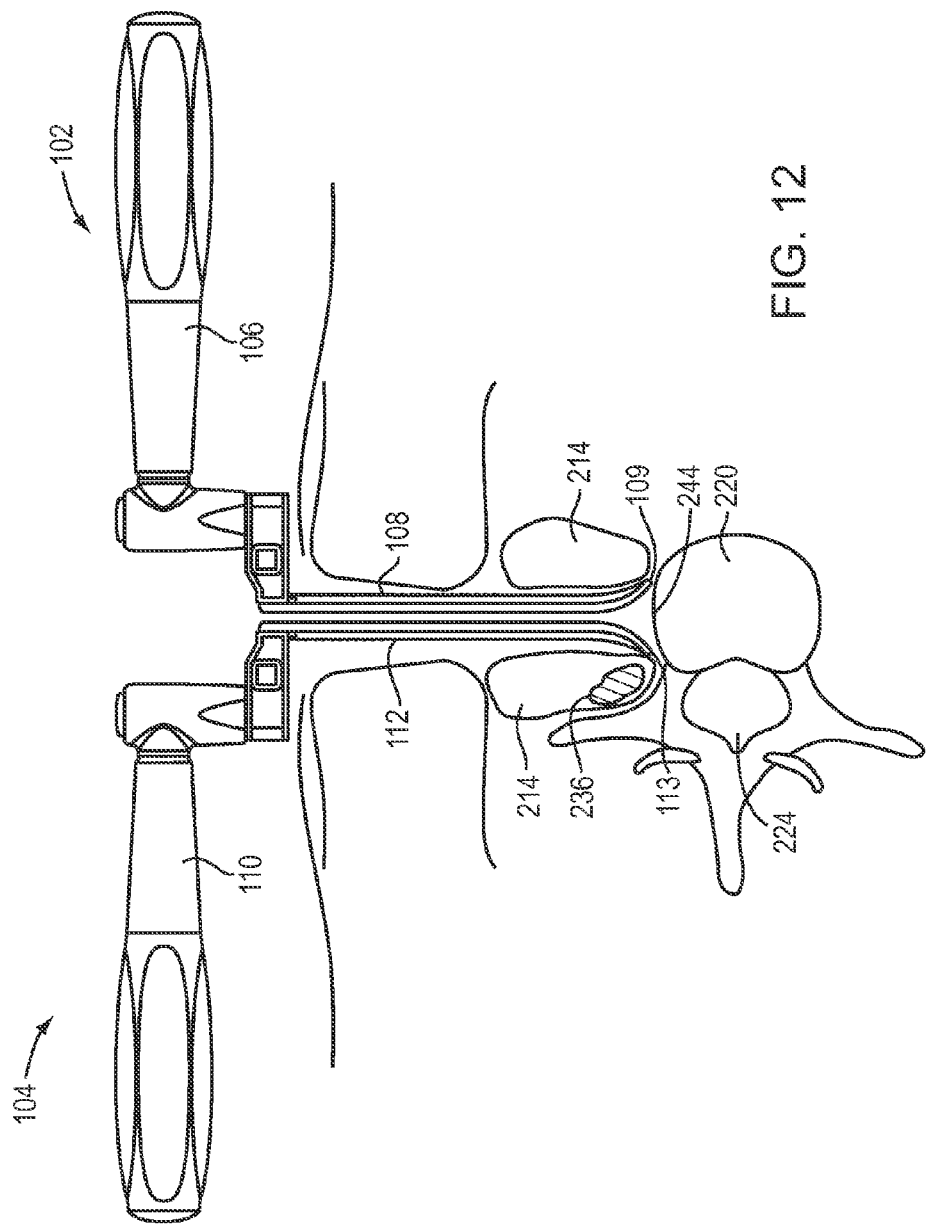
Figure 13:
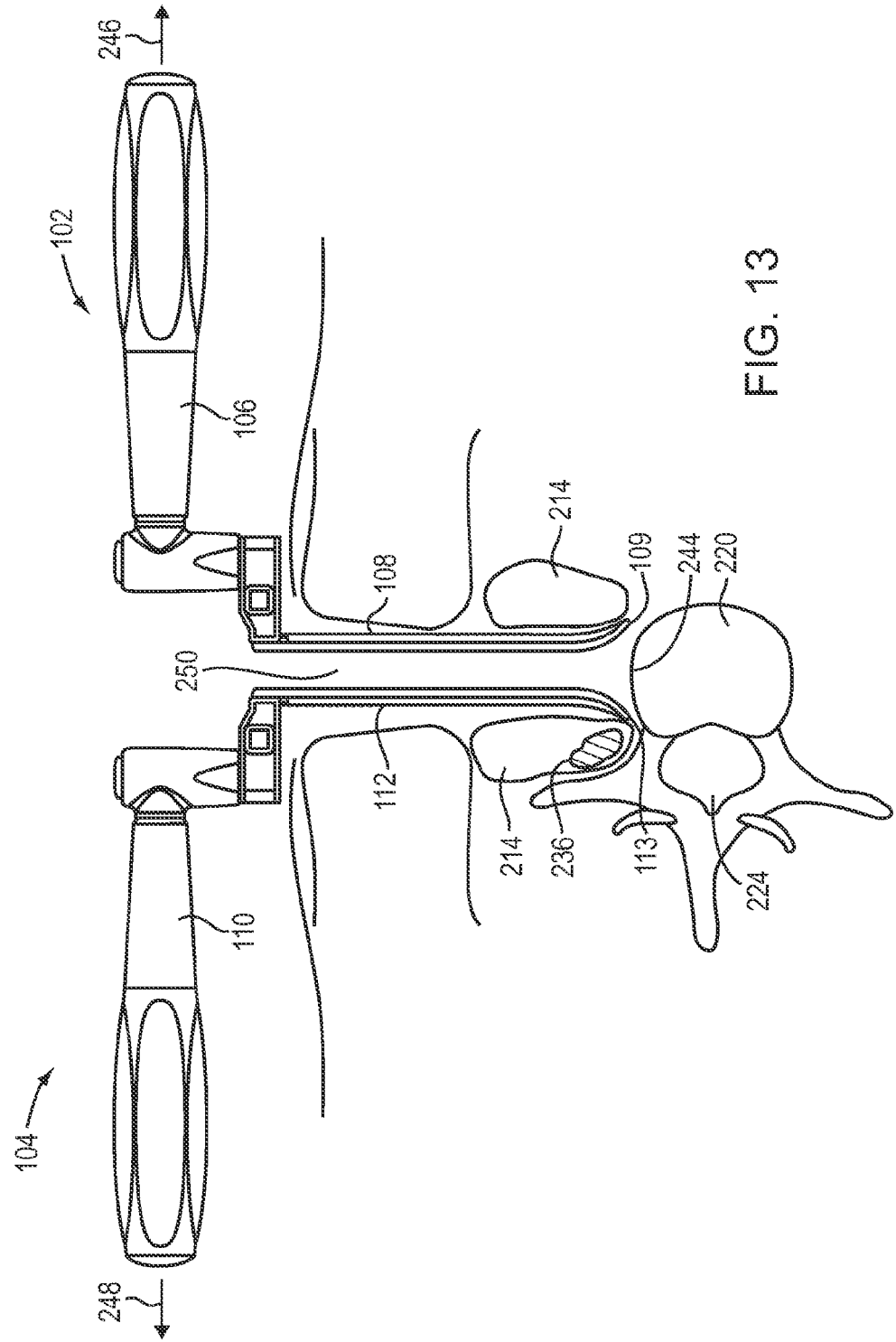

With reference to FIG. 12, after complete dissection of the psoas muscle 214 by the first and second dissecting retractor blades 108, 112, the surgeon positions the first and second dissecting retractor blades 108, 112 substantially parallel to one another and generally perpendicular to the spinal canal 224. As illustrated, the distal ends 109, 113 of the blades 108, 112 are also positioned proximate the intervertebral disc space 220. While the blades 108, 112 are kept substantially parallel to one another and generally perpendicular to the spinal canal 224, the surgeon may separate the blades 108, 112 by moving the handles 106, 110 in the directions of arrows 246, 248, respectively, as shown in FIG. 13. In doing so, the surgeon begins to establish a surgical working channel 250 between the blades 108, 112. The working channel 250 allows for both direct visual and physical access to the working space (or surgical site) 244 at the lateral aspect of the disc space 220.

Figure 14:
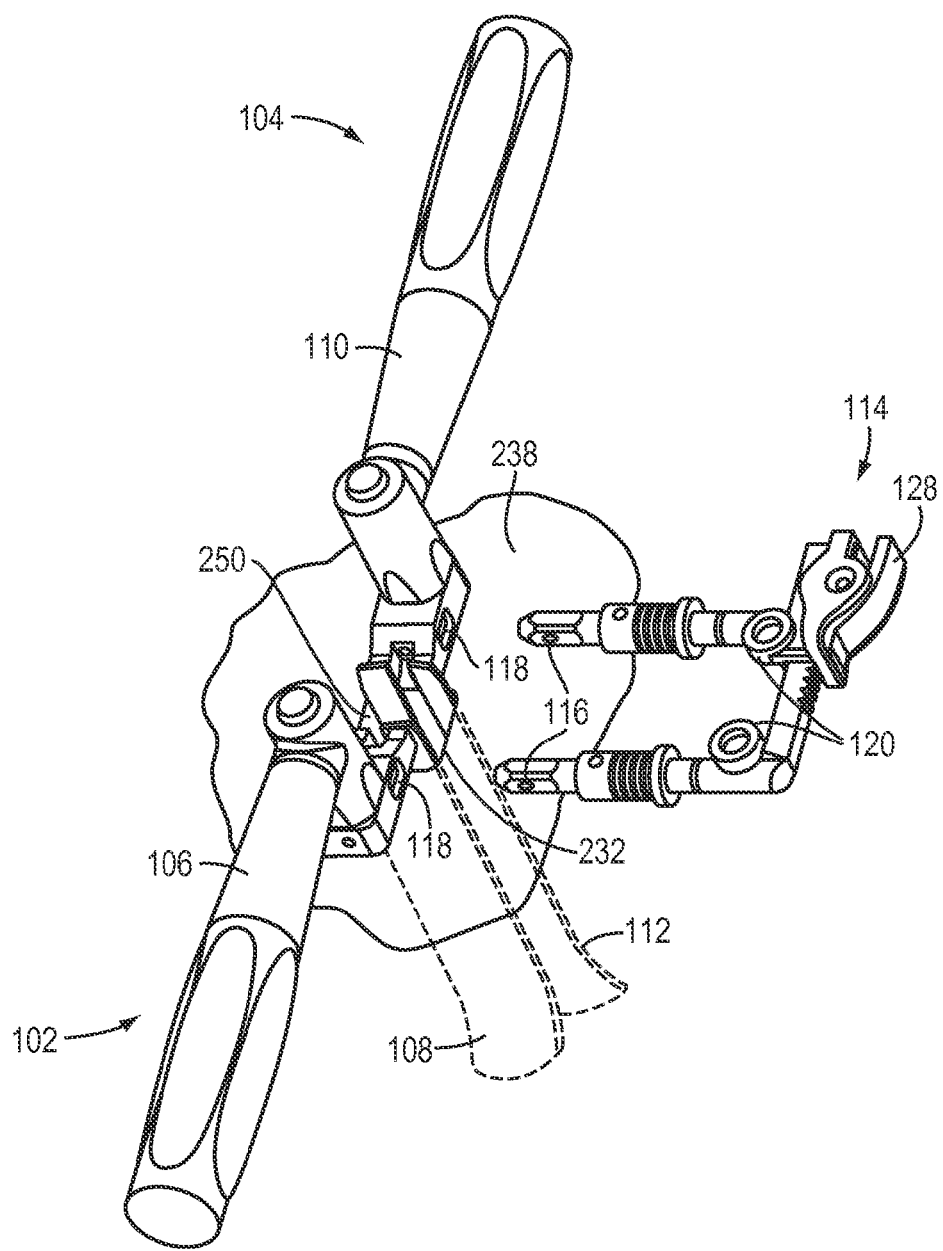
FIG. 14 schematically illustrates a retractor stabilizing frame of a system for accessing an intervertebral disc space readied for coupling to first and second dissecting retractors of the system in accordance with one embodiment of the invention.

Once the first and second dissecting retractor blades 108, 112 have been positioned to begin the creation of the working channel 250, the first and second dissecting retractors 102, 104 may be coupled to one another by coupling the retractor stabilizing frame 114 to both of the retractors 102, 104. In one embodiment, as illustrated in FIG. 14, this is accomplished by continuing to have a first surgeon grasp the handles 106, 110 to maintain the retractors 102, 104 in place, while a second surgeon advances the retractor stabilizing frame 114 in the direction of the retractors 102, 104 and such that the blade attachment fittings 116 of the retractor stabilizing frame 114 mate with the corresponding fittings 118 of the first and second dissecting retractors 102, 104. As previously described, the blade attachment fittings 116 may be snap fittings that the second surgeon snaps into connection with the corresponding fittings 118 of the first and second dissecting retractors 102, 104.

Figure 15:
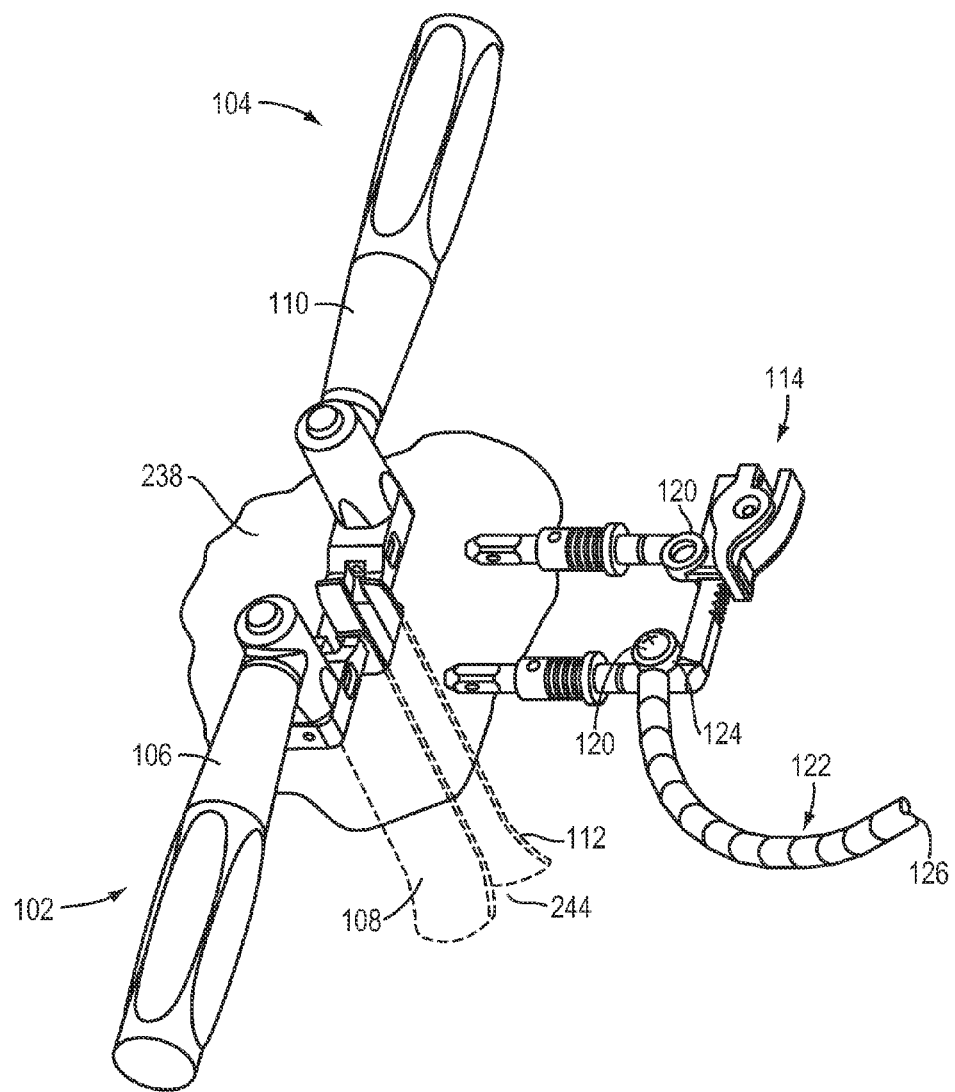
FIG. 15 schematically illustrates a stabilizing arm coupled to the retractor stabilizing frame of FIG. 14 in accordance with one embodiment of the invention.

FIG. 15 schematically illustrates the stabilizing arm 122 coupled to the retractor stabilizing frame 114. In accordance with one embodiment of the invention, the distal end 124 of the stabilizing arm 122 is coupled to (e.g., screwed to, force fit with, etc.) the retractor stabilizing frame 114 at one of the stabilizing arm attachment points 120 prior to coupling the retractor stabilizing frame 114 to the first and second dissecting retractors 102, 104. In fact, the stabilizing arm 122 may be coupled to the retractor stabilizing frame 114 prior to commencing the surgery. Doing so eliminates an intra-operative step and reduces the length of the surgery. Alternatively, the stabilizing arm 122 may be coupled to the retractor stabilizing frame 114 after the surgeons have coupled the retractor stabilizing frame 114 to the first and second dissecting retractors 102, 104.

Figure 16:
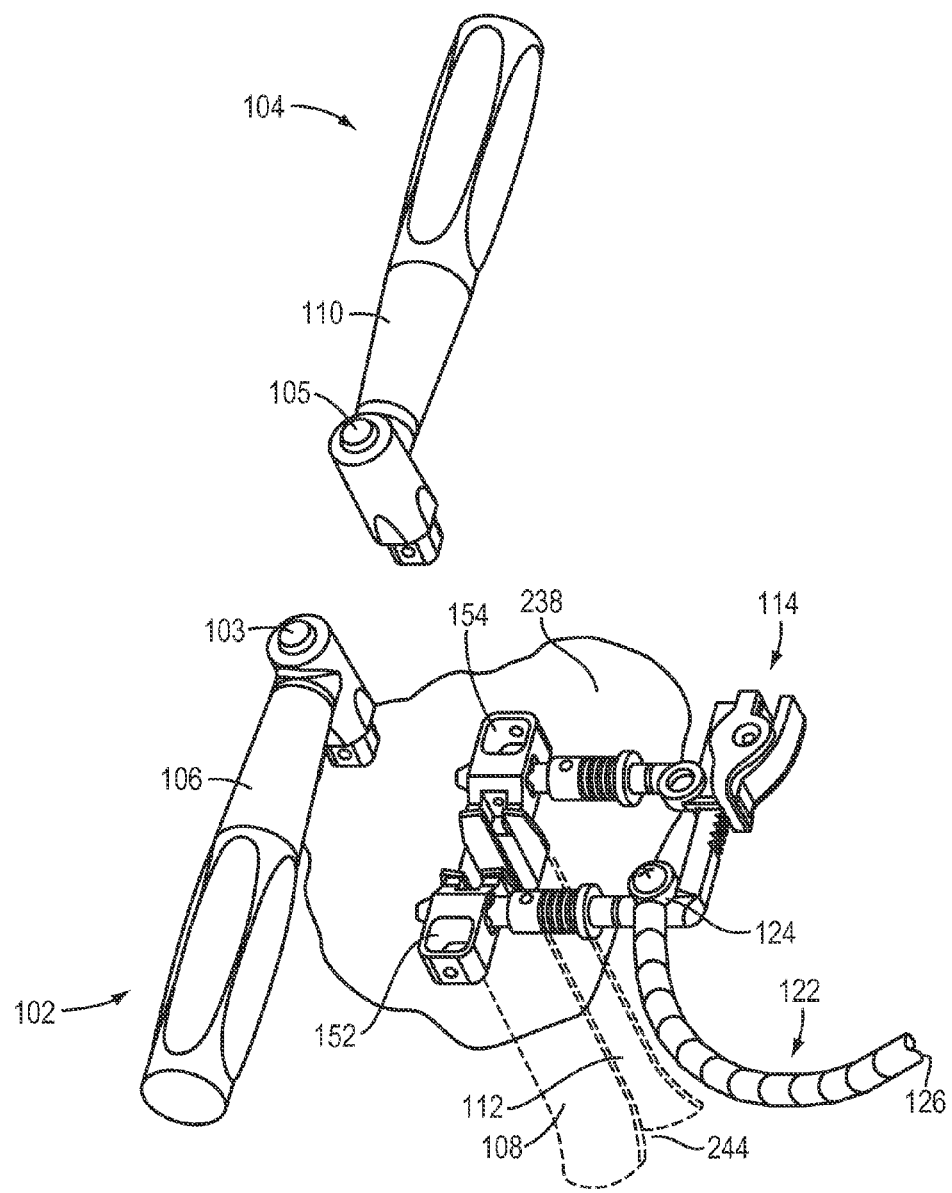
FIG. 16 schematically illustrates first and second handles removed from the first and second dissecting retractors of FIG. 14 in accordance with one embodiment of the invention.

As illustrated in FIG. 16, once the retractor stabilizing frame 114 is coupled to each of the first and second dissecting retractors 102, 104, the surgeon may detach the handles 106, 110 from the first and second dissecting retractors 102, 104 and remove the handles 106, 110 from the surgical field. As previously discussed, the surgeon may do so by disengaging a snap fit, a force fit, or other suitable connection between a handle 106, 110 and an attachment interface 152, 154 of the respective retractor 102, 104. For example, a snap fit may be disengaged by actuating a detachment mechanism 103, 105, such as a push-button release, on each handle 106, 110.

Figure 17:
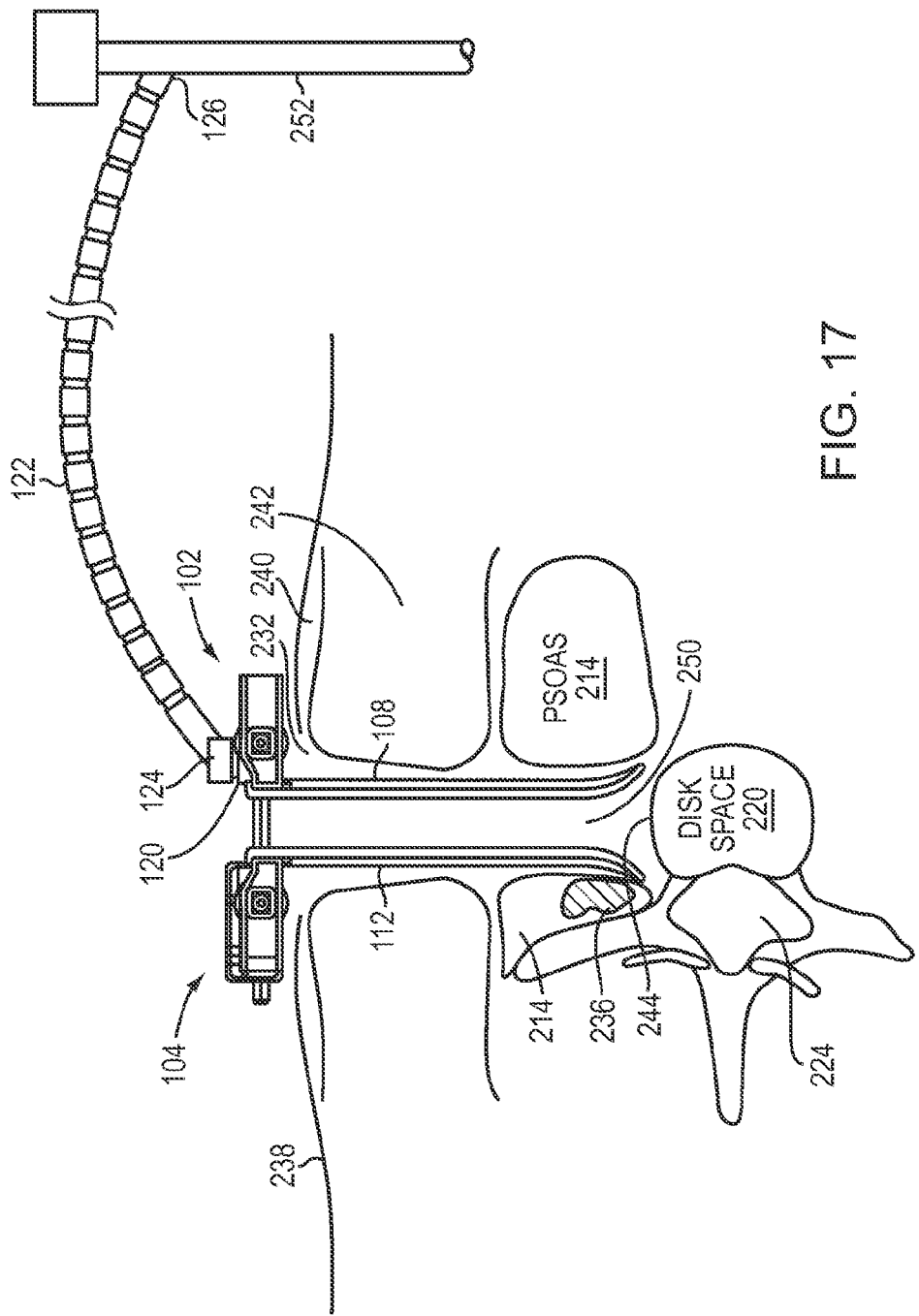
FIG. 17 schematically illustrates a stabilizing arm coupled to the retractor stabilizing frame of FIG. 14 and also to a rigid structure in accordance with one embodiment of the invention.

As illustrated in FIG. 17, to provide further stability to the first and second dissecting retractors 102, 104, the surgeon may also couple the stabilizing arm 122 to a rigid structure 252, such as an operating table. In particular, as previously described, the proximal end 126 of the stabilizing arm 122 may be clamped or connected in another suitable manner by the surgeon to the rigid structure 252. Thereafter, the surgeon may optionally actuate an appropriate mechanism to remove any slack in the stabilizing arm 122. In this way, the initially manually retracted exposure of the working channel 250 is converted to a rigid, stabilized exposure of the working channel 250 without compromising the working channel 250 and without inadvertently closing the incision 232 through the patient's skin level 238, subdermal layer 240, and subdermal tissues 242.

The size of the working channel 250 depicted in FIG. 17 may be adjusted by manipulating the translation mechanism 128 of the refractor stabilizing frame 114. In particular, FIG. 18 depicts the use of the handheld driver 130 to actuate the translation mechanism 128 in accordance with one embodiment of the invention. For simplicity, the stabilizing arm 122 is not shown in FIG. 18. As previously described, in the embodiment illustrated in FIG. 18, the handheld driver 130 is rotated to impart rotation to the pinion 133 and linearly translate the rack of teeth 134, thereby increasing the distance $d_1$ between the legs 115, 117 of the refractor stabilizing frame 114. As the distance $d_1$ increases, so too does the spacing between the first and second blades 108, 112 and, consequently, the size of the working channel 250. The spring-loaded pawl 132 engages the teeth in the rack 134, thereby preventing the distance $d_1$ and the size of the working channel 250 from decreasing.

Figure 19:
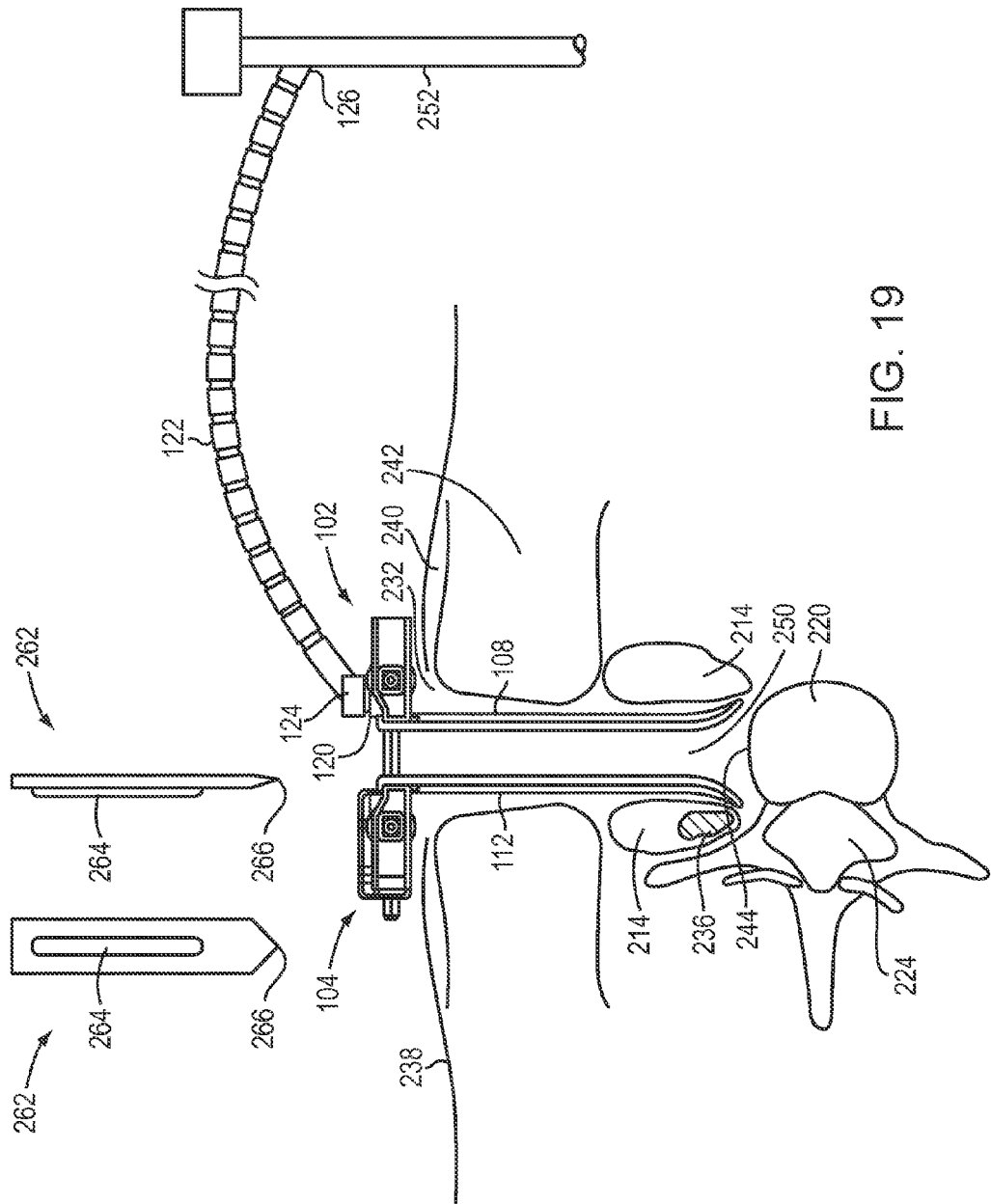
FIGS. 19-20 schematically illustrate the optional use of a keel to fix a blade of a dissecting retractor to the intervertebral disc space of a patient in accordance with one embodiment of the invention.
Figure 20:
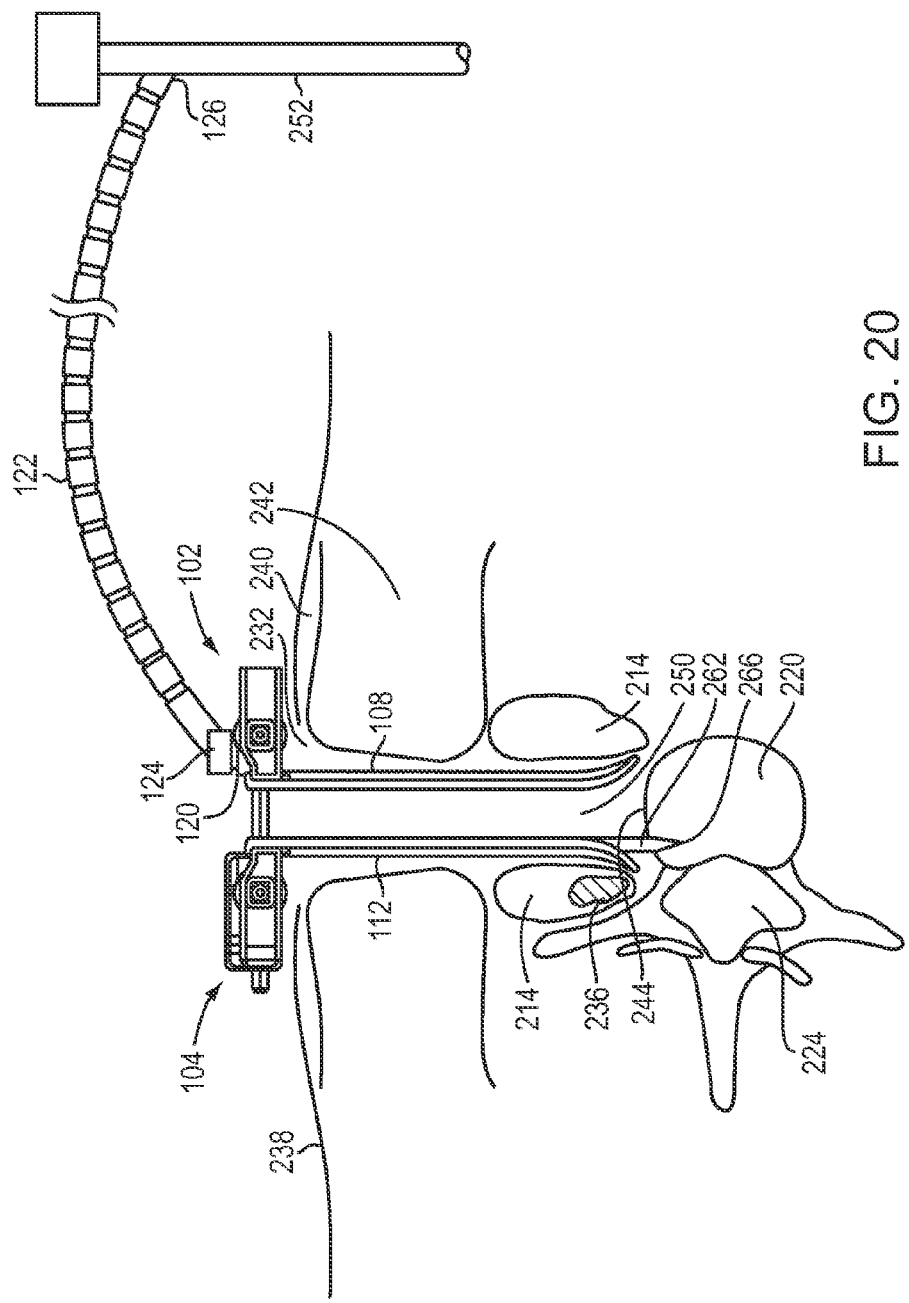

Optionally, once the size of the working channel 250 is established, the surgeon may employ a keel 262 to fix a blade 108, 112 of a dissecting retractor 102, 104 to a disc in the intervertebral disc space 220, and thereby impart even greater stability to the first and second dissecting retractors 102, 104. FIG. 19 depicts front and side views of one such exemplary keel 262. As illustrated, the keel 262 includes a blade guide rail 264 and a sharp distal tip 266 for piercing into and anchoring to a disc in the intervertebral disc space 220. In one illustrative embodiment, the surgeon slides the keel 262 down an inner wall of the second blade 112 of the second dissecting retractor 104, such that the blade guide rail 264 of the keel 262 engages a corresponding blade guide slot in the inner wall of the second blade 112. As illustrated in FIG. 20, the surgeon continues to slide the keel 262 in such a manner and with sufficient force until the sharp distal tip 266 of the keel 262 pierces into a disc in the intervertebral disc space 220. For example, in one embodiment the surgeon advances the sharp distal tip 266 of the keel 262 approximately 1.0 cm to 1.5 cm into the disc.

Figure 21:
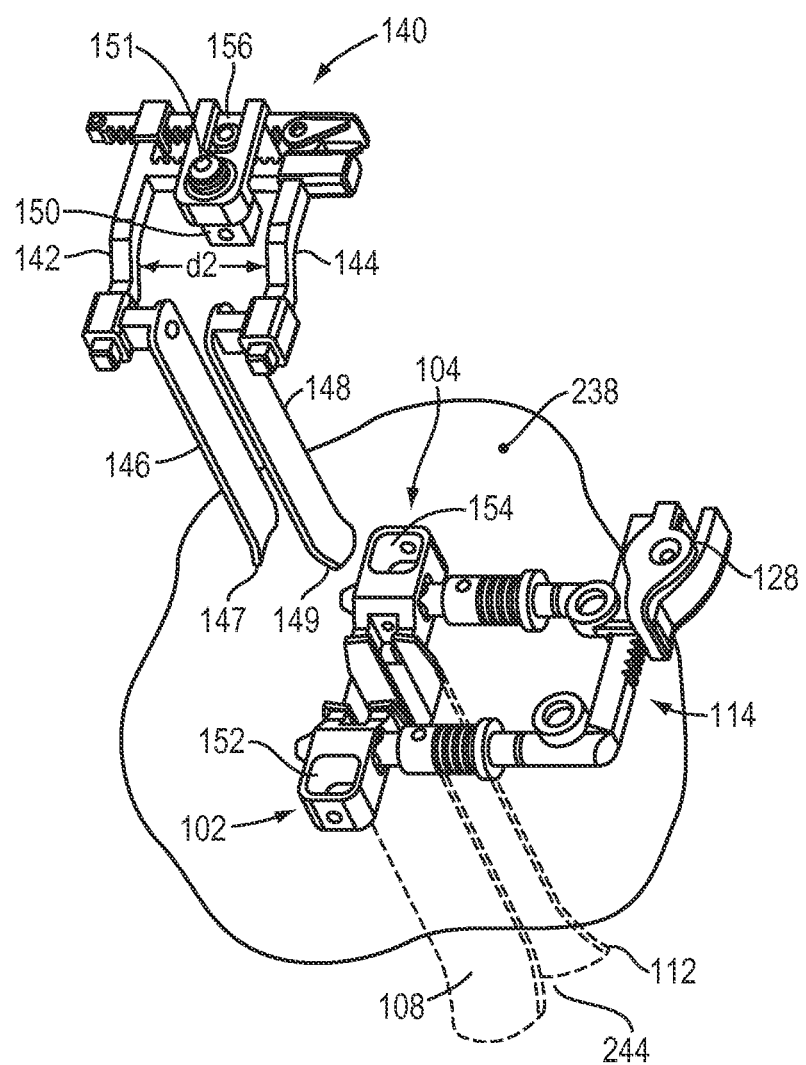
FIG. 21 schematically illustrates an optional blade stabilization frame of a system for accessing an intervertebral disc space positioned over first and second dissecting retractors of the system in accordance with one embodiment of the invention.
Figure 22:
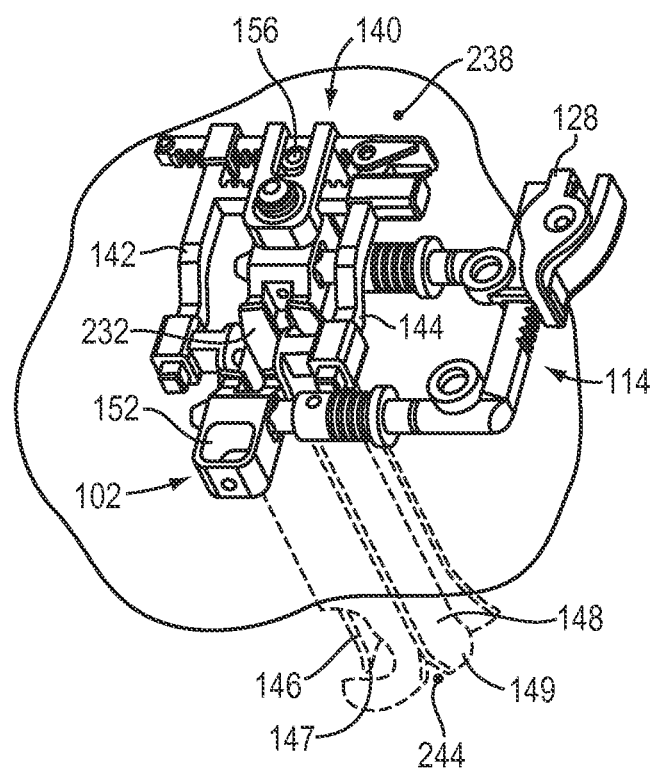
FIG. 22 schematically illustrates the optional blade stabilization frame of FIG. 21 coupled to the second dissecting retractor of FIG. 21 in accordance with one embodiment of the invention.

After the retractor stabilizing frame 114 is coupled to the first and second dissecting retractors 102, 104 and the handles 106, 110 are removed from the retractors 102, 104, the blade stabilization frame 140 may, optionally, be coupled to either the first or second dissecting retractor 102, 104. FIG. 21 depicts one embodiment of the blade stabilization frame 140 positioned over the first and second dissecting retractors 102, 104, which are coupled to the retractor stabilizing frame 114. FIG. 22 depicts the blade stabilization frame 140 coupled to the second dissecting retractor 104 in accordance with one embodiment of the invention. In particular, in FIG. 22, the attachment mechanism 150 (depicted in FIG. 21) of the blade stabilization frame 140 has been coupled to the attachment interface 154 (depicted in FIG. 21) of the second dissecting retractor 104 via, for example, a snap fit, a force fit, or other suitable connection. The blade stabilization frame 140 is thereby coupled, in FIG. 22, to the second dissecting refractor 104. For simplicity, the stabilizing arm 122 is not shown in either FIG. 21 or FIG. 22.

As can be seen in FIG. 22, as a result of coupling the blade stabilization frame 140 to the second dissecting refractor 104, the third and fourth blades 146, 148 of the blade stabilization frame 140 have been directed through the skin incision 232 such that the distal ends 147, 149 of the third and fourth blades 146, 148 are positioned proximate the surgical site 244 (e.g., the intervertebral disc space 220).

In a similar fashion to the approach described above (with reference to FIG. 18) for the retractor stabilizing frame 114, a driver similar to the driver 130 may be employed to manipulate the translation mechanism 156 of the blade stabilization frame 140 to increase the distance $d_2$ (see FIG. 21) between the legs 142, 144 of the blade stabilization frame 140, thereby also increasing a spacing between the third and fourth blades 146, 148 and, consequently, the size of the working channel 250. In fact, through use of the translation mechanism 128 of the retractor stabilizing frame 114 and the translation mechanism 156 of the blade stabilization frame 140, multiple dimensions of the working channel 250 may be adjusted to provide any one of a number of sizes for the working channel 250 that may be required by the surgeon.

Optionally, in one embodiment, the third and fourth blades 146, 148 of the blade stabilization frame 140 also feature a "toe-in" capability. In particular, as illustrated in FIGS. 23A and 23B, a distance between the distal ends 147, 149 of the third and fourth blades 146, 148 may be increased, thereby also expanding a distal portion of the working channel 250. To facilitate such a "toe-in" functionality, the blade stabilization frame 140 may include buttons 160, 164 that may be depressed in order to release a blade rotation housing 168, 172 from its respective leg 142, 144, and/or lock the blade rotation housing 168, 172 to its respective leg 142, 144. For example, as illustrated in FIG. 23B, the surgeon may depress the button 164 to release the blade rotation housing 172 from the leg 144, may then rotate the blade rotation housing 172 (and thus the fourth blade 148) in a counter-clockwise direction about the leg 144 to increase a distance between the distal ends 147, 149 of the third and fourth blades 146, 148, and may then depress the button 164 to again lock the blade rotation housing 172 to the leg 144. The surgeon may also, in a similar fashion, rotate the blade rotation housing 168 (and thus the third blade 146) in a clockwise direction about the leg 142. In such a fashion, the surgeon may expand a distal portion of the working channel 250.

Figure 24:
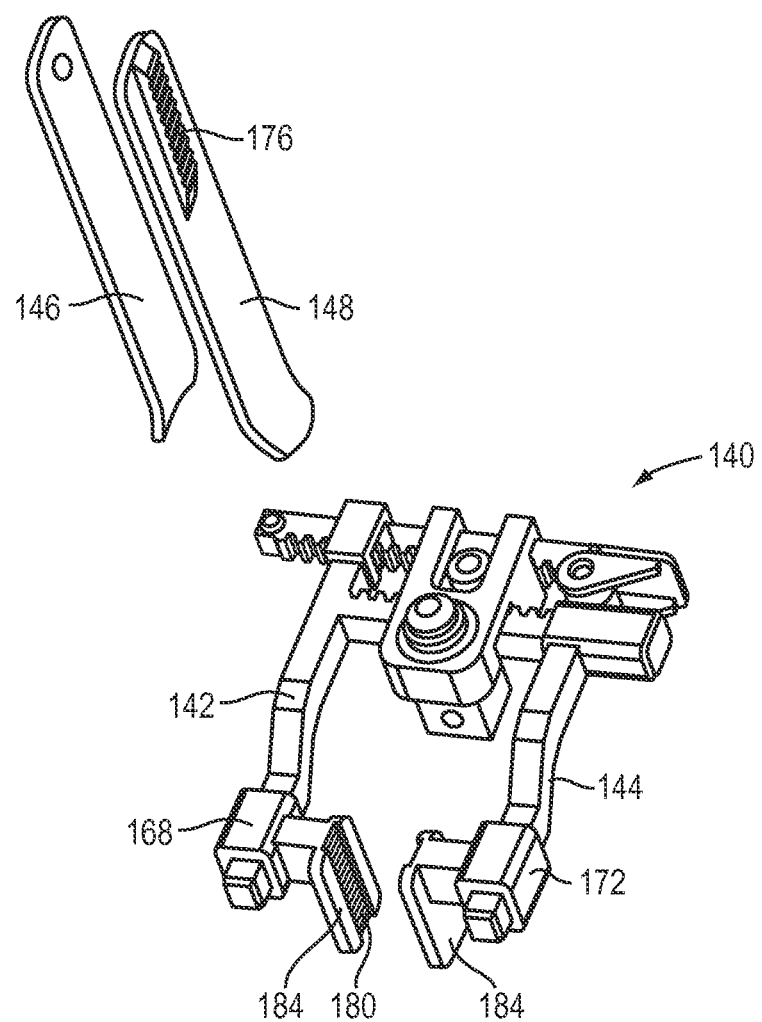
FIGS. 24, 25A, and 25B schematically illustrate a "lengthwise adjustment" capability of the blades of the optional blade stabilization frame of FIG. 21 in accordance with one embodiment of the invention.
Figure 25B:
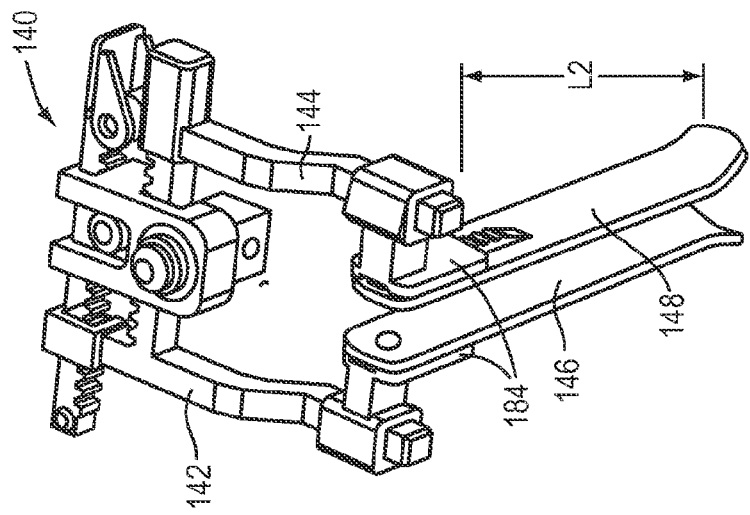
Figure 25A:
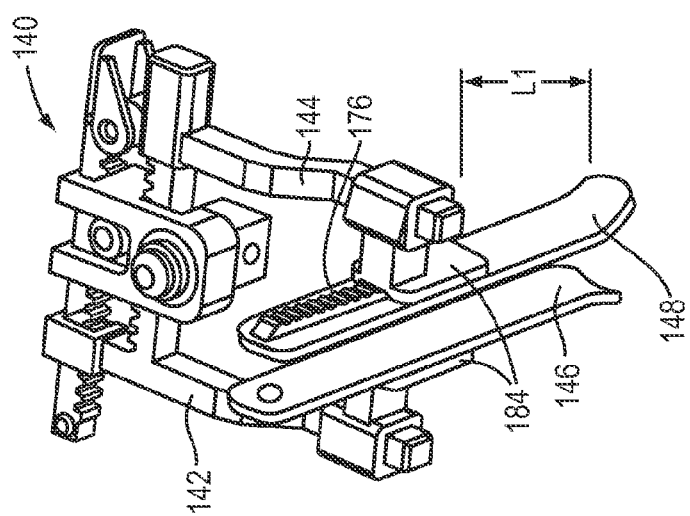

Optionally, in order to maintain contact with the patient's spine when the third and fourth blades 146, 148 are rotated about the legs 142, 144 of the blade stabilization frame 140 as described above, the third and fourth blades 146, 148 may also be adjustable in a lengthwise fashion. For example, as illustrated in FIG. 24, each blade 146, 148 may include a blade translation track 176 permitting the blade 146, 148 to move downwards and upwards along a blade translation track adapter 180 of a corresponding blade fitting 184. In particular, the blade translation track 176 of each blade 146, 148 may include detents that mate with corresponding features of the blade translation track adapter 180 to maintain the blade 146, 148 in a fixed, yet adjustable, position during use. In greater detail, and as illustrated in FIGS. 25A and 25B, each blade 146, 148 may be inserted into its respective blade fitting 184 and be independently adjusted downwards or upwards to vary a length L of the blade 146, 148 below the patient's skin level 238. For example, the length $L_2$ of the blades 146, 148 below the patient's skin level 238 in FIG. 25B is greater than the length $L_1$ of the blades 146, 148 below the patient's skin level 238 in FIG. 25A. Accordingly, after the surgeon has rotated the blades 146, 148 about the legs 142, 144 of the blade stabilization frame 140 as described above, the surgeon may also increase the length L of the blades 146, 148 below the patient's skin level 238 in order to maintain contact with the patient's spine.

As will be understood by those of ordinary skill in the art, the above-described "toe-in" functionality and lengthwise adjustment of the blades may be independently employed or used together on any one of the first, second, third, and fourth blades 108, 112, 146, 148. For example, while the "toe-in" functionality and lengthwise adjustment of the blades has been described above with reference to the third and fourth blades 146, 148 of the blade stabilization frame 140, those of ordinary skill in the art will appreciate that the first and second blades 108, 112 may also feature the "toe-in" capability and/or have their length adjusted below the patient's skin level 238 in the same manner as the third and fourth blades 146, 148.

Figure 26:
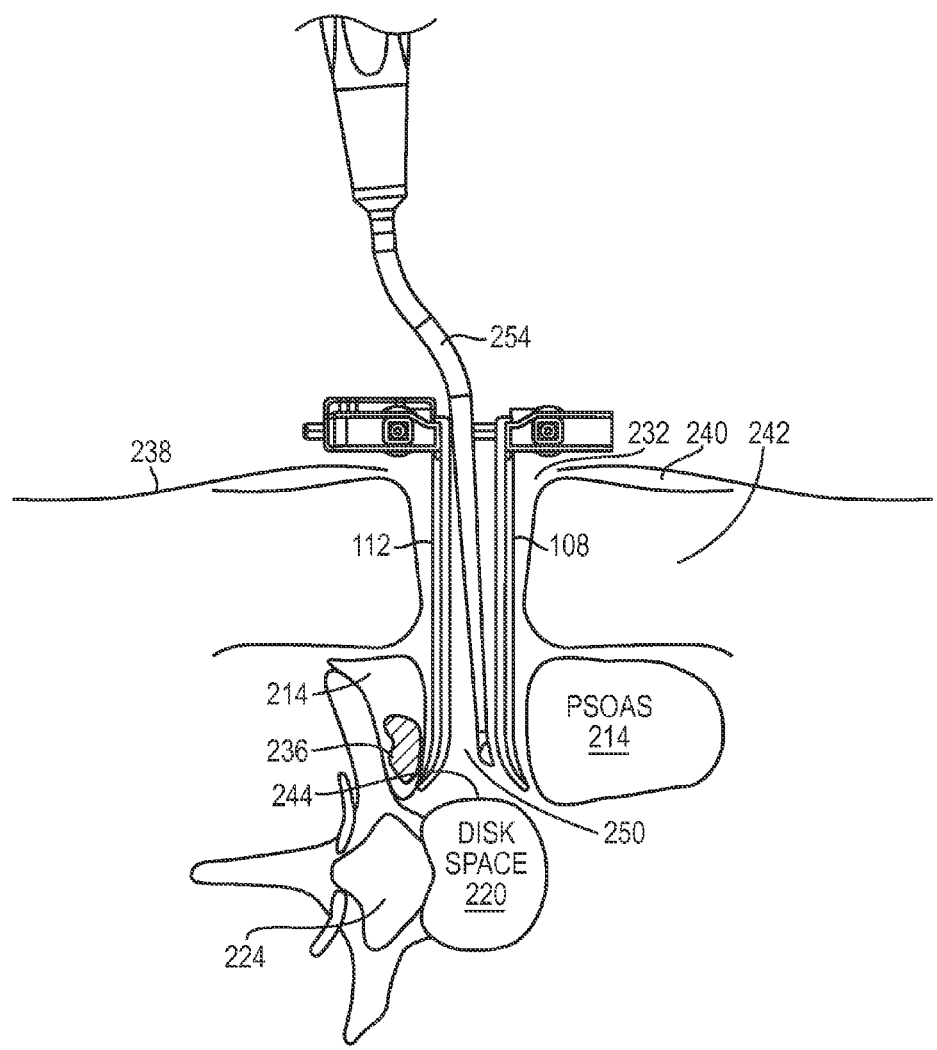
FIG. 26 schematically illustrates the use of a discectomy instrument in accordance with one embodiment of the invention.
Figure 27:
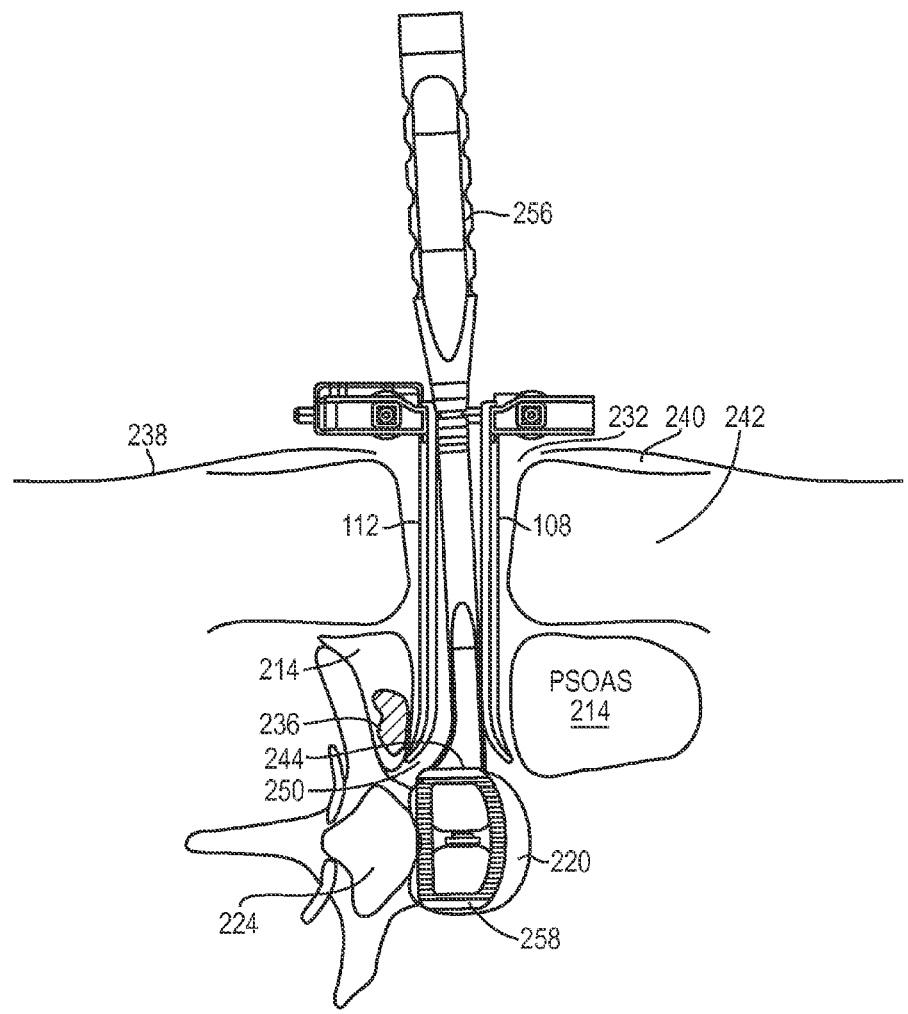
FIG. 27 schematically illustrates the use of an intervertebral fusion cage inserter to deliver an intervertebral fusion cage in accordance with one embodiment of the invention.
Figure 28:
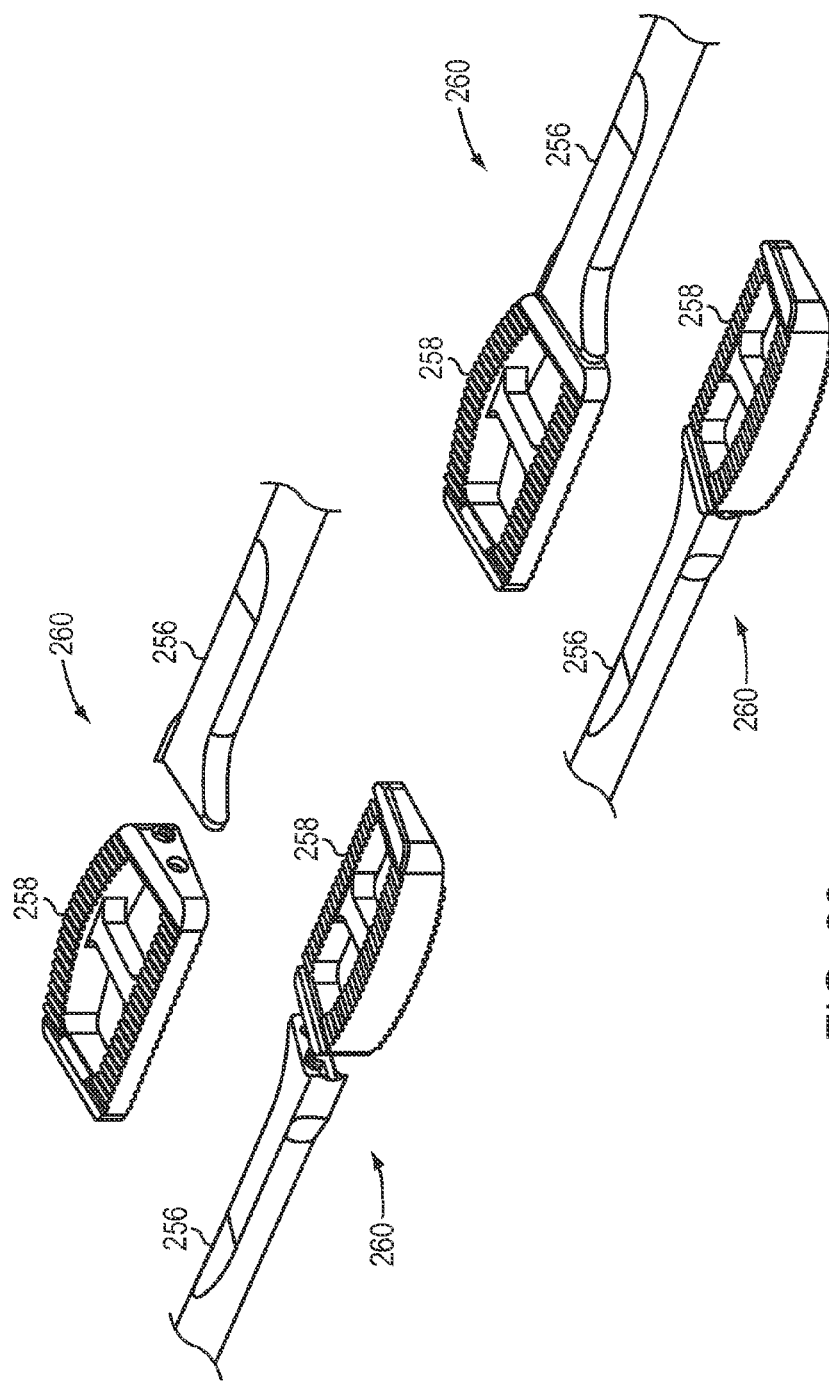
FIG. 28 schematically illustrates various views of a distal end of the intervertebral fusion cage inserter of FIG. 27 and of how it couples to and releases the intervertebral fusion cage of FIG. 27 in accordance with various embodiments of the invention.

Once the retractor stabilizing frame 114 (and, optionally, the blade stabilization frame 140) has been coupled to the first and/or second dissecting retractors 102, 104, and the first and second dissecting retractor blades 108, 112 (and, optionally, the third and fourth blades 146, 148 of the blade stabilization frame 140) have established the working channel 250, various surgical instruments may be directed through the skin incision 232 and the stabilized working channel 250 to the distal surgical site 244, such as the intervertebral disc space 220, to perform various tasks required by the surgeon. In addition, various surgical implants may also be delivered through the skin incision 232 and the stabilized working channel 250 to the distal surgical site 244, such as the intervertebral disc space 220. For example, as illustrated in FIG. 26, a discectomy instrument 254 may be directed to the intervertebral disc space 220 to remove herniated disc material, as will be understood by one of ordinary skill in the art. As another example, and with reference to FIG. 27, an intervertebral fusion cage inserter 256 may be directed to the intervertebral disc space 220 to deliver an intervertebral fusion cage 258, as will also be understood by one of ordinary skill in the art. Various exemplary views of a distal end 260 of the intervertebral fusion cage inserter 256 and of how it couples to and releases the intervertebral fusion cage 258 are shown in FIG. 28.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive. Furthermore, the configurations described herein are intended as illustrative and in no way limiting. Similarly, although physical explanations have been provided for explanatory purposes, there is no intent to be bound by any particular theory or mechanism, or to limit the claims in accordance therewith.

INCORPORATION BY REFERENCE

The entire disclosures of each of the patent documents and scientific articles cited herein are incorporated by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for accessing an intervertebral disc space in a body of a patient, the method comprising:
   making an incision in a region of the patient's body that permits access to a psoas muscle;
   directing a blade of a first dissecting retractor through the incision and such that a distal end of the first dissecting retractor blade is positioned proximate the intervertebral disc space; directing, independently of the first dissecting retractor blade, a blade of a second dissecting retractor through the incision and such that a distal end of the second dissecting retractor blade is positioned proximate the intervertebral disc space, the first and second dissecting retractor blades employed during their placement within the patient's body in a tissue dissection process to gain access to the intervertebral disc space; and
   following the positioning of the distal ends of the first and second dissecting retractor blades proximate the intervertebral disc space, coupling the first and second dissecting retractors to one another.

2. The method of claim 1 further comprising manually palpating the psoas muscle subsequent to making the incision in the region of the patient's body.

3. The method of claim 1, wherein directing the first dissecting retractor blade comprises directing the first dissecting retractor blade anterior to, or through, the psoas muscle.

4. The method of claim 1, wherein directing the second dissecting retractor blade comprises positioning the second dissecting retractor blade posterior to the first dissecting retractor blade.

5. The method of claim 1, wherein the first and second dissecting retractor blades are both directed to avoid a region in the psoas muscle comprising a lumbar plexus nerve group.

6. The method of claim 1, wherein coupling the first and second dissecting retractors to one another comprises coupling a retractor stabilizing frame to both the first and second dissecting retractors.

7. The method of claim 6 further comprising removing a handle from each of the first and second dissecting retractors subsequent to coupling the retractor stabilizing frame to each of the first and second dissecting retractors.

8. The method of claim 6, further comprising coupling a stabilizing arm to the retractor stabilizing frame and to a rigid structure.

9. The method of claim 8, wherein the rigid structure comprises an operating table.

10. The method of claim 6, wherein the retractor stabilizing frame comprises a translation mechanism for adjusting a spacing between the first and second dissecting retractor blades.

11. The method of claim 10 further comprising adjusting a size of a working channel defined within the patient's body by manipulating the translation mechanism.

12. The method of claim 1 further comprising directing third and fourth blades through the incision and such that distal ends of the third and fourth blades are positioned proximate the intervertebral disc space.

13. The method of claim 12, wherein the third and fourth blades are both coupled to a blade stabilization frame.

14. The method of claim 13 further comprising coupling the blade stabilization frame to at least one of the first and second dissecting retractors.

15. The method of claim 13, wherein the blade stabilization frame comprises a translation mechanism for adjusting a spacing between the third and fourth blades.

16. The method of claim 15 further comprising adjusting a size of a working channel defined within the patient's body by manipulating the translation mechanism.

17. The method of claim 1 further comprising directing a surgical instrument through the incision and to the intervertebral disc space.

18. The method of claim 17, wherein the surgical instrument comprises an intervertebral fusion cage inserter.

19. The method of claim 1 further comprising delivering a surgical implant through the incision and to the intervertebral disc space.

20. The method of claim 19, wherein the surgical implant comprises an intervertebral fusion cage.

21. The method of claim 1 further comprising targeting a desired surgical level and sizing lengths of the first and second dissecting retractor blades prior to making the incision.

22. The method of claim 21, wherein a measurement caliper is employed to target the desired surgical level and size the lengths of the first and second dissecting retractor blades.

* * * * *